United States Patent
Ino et al.

(10) Patent No.: US 8,147,504 B2
(45) Date of Patent: Apr. 3, 2012

(54) APPARATUS AND METHODS FOR DELIVERING FASTENERS DURING VALVE REPLACEMENT

(75) Inventors: Takashi Harry Ino, San Jose, CA (US); Michael J. Drews, Palo Alto, CA (US); Donnell W. Gurskis, Belmont, CA (US); Dwight J. Knab, Jr., Newark, CA (US)

(73) Assignee: Medtronic, Inc., Minneapolis, MN (US)

( * ) Notice: Subject to any disclaimer, the term of this patent is extended or adjusted under 35 U.S.C. 154(b) by 892 days.

(21) Appl. No.: 12/115,543

(22) Filed: May 5, 2008

(65) Prior Publication Data

US 2009/0036903 A1 Feb. 5, 2009

Related U.S. Application Data

(60) Provisional application No. 60/916,283, filed on May 5, 2007.

(51) Int. Cl.
 A61B 17/10 (2006.01)
 B25C 5/04 (2006.01)
 B25C 5/08 (2006.01)

(52) U.S. Cl. ............ 606/143; 606/142; 227/175.1; 227/82

(58) Field of Classification Search ............... 606/139, 606/142, 143, 219, 75, 153; 227/175.1–182.1, 227/82, 85
See application file for complete search history.

(56) References Cited

U.S. PATENT DOCUMENTS

| | | | | |
|---|---|---|---|---|
| 4,086,926 A | * | 5/1978 | Green et al. | 606/143 |
| 4,246,903 A | * | 1/1981 | Larkin | 606/143 |
| 4,496,090 A | * | 1/1985 | Crevier et al. | 227/19 |
| 4,509,518 A | * | 4/1985 | McGarry et al. | 606/143 |
| 4,624,254 A | * | 11/1986 | McGarry et al. | 606/143 |
| 4,637,395 A | * | 1/1987 | Caspar et al. | 606/143 |
| 4,671,278 A | * | 6/1987 | Chin | 606/143 |
| 4,821,721 A | * | 4/1989 | Chin et al. | 606/143 |
| 4,854,317 A | * | 8/1989 | Braun | 606/143 |
| 4,874,122 A | * | 10/1989 | Froelich et al. | 227/19 |
| 4,899,745 A | * | 2/1990 | Laboureau et al. | 606/142 |
| 4,983,176 A | * | 1/1991 | Cushman et al. | 606/151 |
| 5,035,692 A | * | 7/1991 | Lyon et al. | 606/143 |
| 5,192,288 A | * | 3/1993 | Thompson et al. | 606/143 |
| 5,207,692 A | * | 5/1993 | Kraus et al. | 606/143 |
| 5,242,457 A | * | 9/1993 | Akopov et al. | 606/144 |
| 5,269,792 A | * | 12/1993 | Kovac et al. | 606/158 |
| 5,282,808 A | * | 2/1994 | Kovac et al. | 606/143 |
| 5,413,584 A | * | 5/1995 | Schulze | 606/219 |
| 5,425,489 A | * | 6/1995 | Shichman et al. | 227/108 |
| 5,439,468 A | * | 8/1995 | Schulze et al. | 606/143 |
| 5,456,400 A | * | 10/1995 | Shichman et al. | 227/176.1 |
| 5,542,949 A | * | 8/1996 | Yoon | 606/143 |
| 5,547,474 A | * | 8/1996 | Kloeckl et al. | 606/143 |
| 5,618,311 A | * | 4/1997 | Gryskiewicz | 606/216 |
| 5,626,585 A | * | 5/1997 | Mittelstadt et al. | 606/143 |
| 5,674,231 A | * | 10/1997 | Green et al. | 606/142 |

(Continued)

*Primary Examiner* — Julian Woo
*Assistant Examiner* — Christopher L Templeton

(57) ABSTRACT

A fastener delivery tool includes a belt including pairs of features for releasably engaging tines of respective fasteners in a relaxed state defining a loop. The tool includes a loading chamber for receiving a fastener from the belt, a retaining member for limiting movement of the fastener within the loading chamber, an ejection track communicating with the loading chamber, a handle including an actuator, and a tongue and pusher member coupled to the actuator. Activation of the actuator advances the tongue to transform the fastener from the relaxed state to a U-shaped constrained state, and advances the pusher member to direct the fastener from the loading chamber down the ejection track.

30 Claims, 33 Drawing Sheets

U.S. PATENT DOCUMENTS

| | | | |
|---|---|---|---|
| 5,715,987 A * | 2/1998 | Kelley et al. | 227/175.1 |
| 5,843,097 A * | 12/1998 | Mayenberger et al. | 606/143 |
| 6,352,541 B1 * | 3/2002 | Kienzle et al. | 606/143 |
| 6,464,710 B1 * | 10/2002 | Foster | 606/158 |
| 6,702,826 B2 * | 3/2004 | Liddicoat et al. | 606/151 |
| 6,767,356 B2 * | 7/2004 | Kanner et al. | 606/213 |
| 6,837,895 B2 * | 1/2005 | Mayenberger | 606/142 |
| 7,056,330 B2 * | 6/2006 | Gayton | 606/219 |
| 7,179,265 B2 * | 2/2007 | Manetakis et al. | 606/142 |
| 7,344,544 B2 * | 3/2008 | Bender et al. | 606/139 |
| 7,473,258 B2 * | 1/2009 | Clauson et al. | 606/139 |
| 7,533,790 B1 * | 5/2009 | Knodel et al. | 227/175.1 |
| 7,572,266 B2 * | 8/2009 | Young et al. | 606/143 |
| 7,594,920 B2 * | 9/2009 | Kayan et al. | 606/143 |
| 7,744,610 B2 * | 6/2010 | Hausen | 606/142 |
| 2002/0087169 A1 * | 7/2002 | Brock et al. | 606/139 |
| 2005/0080454 A1 * | 4/2005 | Drews et al. | 606/221 |
| 2005/0107810 A1 * | 5/2005 | Morales et al. | 606/143 |
| 2005/0107871 A1 * | 5/2005 | Realyvasquez et al. | 623/2.11 |
| 2006/0122634 A1 * | 6/2006 | Ino et al. | 606/142 |
| 2008/0119875 A1 * | 5/2008 | Ino et al. | 606/142 |

* cited by examiner

FIG. 8(b) Section A-A

FIG. 9(b) Section B-B

FIG. 10(b) Section C-C

FIG. 11(b) Section D-D

FIG. 12(b) Section E-E

FIG. 13(b) Section F-F

FIG. 14(b) Section G-G

APPARATUS AND METHODS FOR DELIVERING FASTENERS DURING VALVE REPLACEMENT

RELATED APPLICATION DATA

This application claims benefit of provisional application Ser. No. 60/916,283, filed May 5, 2007, the entire disclosure of which is expressly incorporated by reference herein.

FIELD OF THE INVENTION

The invention relates generally to apparatus and methods for fastening devices to tissue or other devices, and, more particularly, to apparatus and methods for delivering fasteners during heart valve replacement, placement of other prostheses, or repair of body organs in general and vascular surgery, such as wound closure, anastomosis, hernia repair, and grafting procedures for aneurysm repair.

BACKGROUND

Prosthetic heart valves have been used to replace defective human valves in patients. A prosthetic valve generally includes a sewing ring or suture cuff that may be attached to and/or extend around a valve member. The sewing ring may be made from a biocompatible fabric and/or other material through which a needle and suture may pass. The sewing ring may be part of a single piece prosthetic valve, or may be part of a multiple piece prosthetic valve assembly.

In a typical aortic valve replacement procedure, the aorta may be incised and the defective valve leaflets removed, leaving a desired placement site that may include a fibrous tissue layer or tissue annulus. Needles carrying sutures may be directed through the fibrous tissue or desired placement site within the tissue annulus to form an array of sutures. Free ends of the sutures may be extended out of the thoracic cavity and laid, spaced apart, on the patient's body.

The needles and sutures may then be threaded individually through a sewing ring, typically delivering between twelve and twenty (12-20) sutures through the sewing ring. Once the sutures have been directed through the sewing ring, the sutures may be pulled up taught and the sewing ring may be slid over the sutures or "parachuted" down into place adjacent the placement site tissue. The sewing ring may then be secured in place by knot tying knots in the sutures. This procedure is time consuming as doctors often use three to ten knots per suture.

If the sewing ring is separate from a valve member of a multiple component prosthesis, the valve member may be introduced into the placement site, and secured to the sewing ring. The sutures may be tied, not only to secure the sewing ring to the biological mass, but to secure the valve member to the sewing ring (and consequently, to the tissue annulus).

During heart valve replacement procedures, the patient may be on cardiopulmonary bypass (CPB), which may reduce the patient's oxygen level and/or create non-physiological blood flow dynamics. The longer a patient is on CPB, the greater the risk for long-term or even permanent health damage. Existing suturing techniques extend the duration of CPB and, consequently, increase the health risks due to the patient. Furthermore, the fixturing force created by suturing varies significantly from suture to suture, even for the same medical professional.

Sewing rings can also be tedious and time consuming to secure to a valve orifice. To assemble multiple component heart valves, for example, one component has to be sewn into another in vivo, resulting in a complex and time consuming process. The complexity of the procedure also provides a greater opportunity for mistakes and requires a patient to be on cardiopulmonary bypass for a lengthy period.

SUMMARY OF THE INVENTION

The present invention is directed to apparatus and methods for fastening devices to tissue and/or other devices, and, more particularly, to apparatus and methods for delivering fasteners during heart valve replacement. For example, the apparatus and methods may involve deploying one or more fasteners to secure a prosthesis to surrounding tissue, or to secure one prosthesis to another, or a portion of a prosthesis to a coordinating prosthesis.

In accordance with one embodiment, a fastener delivery tool is provided that includes a belt including pairs of features for releasably engaging tines of respective fasteners in a relaxed state; a loading chamber for receiving a fastener from the belt in the relaxed state; a releasable retaining member for limiting movement of the fastener within the loading chamber; an ejection track communicating with the loading chamber; a handle including an actuator; and a tongue and a pusher member coupled to the actuator, activation of the actuator advancing the tongue to engage the tines so as to transform the fastener from the relaxed state to a constrained state and advancing the pusher member to advance the fastener from the loading chamber down the ejection track.

In accordance with another embodiment, a fastener delivery tool is provided that includes a housing including an actuator; a cartridge assembly extending from the housing and carrying a plurality of fasteners, the cartridge assembly comprising a belt comprising pairs of features releasably engaging tines of respective fasteners in a relaxed state, each of the fasteners defining a loop between the tines in the relaxed state; a loading chamber for successively receiving a fastener from the belt in the relaxed state; a retaining member for limiting movement of the fastener received within the loading chamber; an ejection track communicating with the loading chamber; and a tongue and a pusher member coupled to the actuator. In one embodiment, activation of the actuator advances the tongue to engage the tines so as to transform the fastener received within the loading chamber from the relaxed state to a U-shaped constrained state, advances the pusher member to advance the fastener from the loading chamber down the ejection track, and advances the belt to deliver another fastener within the loading chamber.

In accordance with yet another embodiment, a fastener delivery tool is provided that includes a housing including an actuator; an elongate shaft extending from the housing and terminating in a distal tip, the shaft comprising a belt assembly therein comprising pairs of features releasably engaging tines of respective fasteners in a relaxed state, each of the fasteners defining a loop between the tines in the relaxed state; a loading chamber in the distal tip for successively receiving a fastener from the belt in the relaxed state; a retaining member for limiting movement of the fastener received within the loading chamber; an ejection track communicating with the loading chamber; and a tongue and a pusher member coupled to the actuator. In one embodiment, activation of the actuator advances the tongue to engage the tines so as to transform the fastener received within the loading chamber from the relaxed state to a U-shaped constrained state, and advances the pusher member to advance the fastener from the loading chamber down the ejection track. The actuator may advance the belt to deliver a fastener within the loading chamber before or after the other actuation steps.

In accordance with still another embodiment, a method is provided delivering a fastener using a tool including a belt assembly carrying a plurality of fasteners, the method including advancing the belt assembly to deliver a first fastener from the belt assembly onto a retaining member, the fastener comprising a pair of tines; advancing a tongue in the delivery tool relative to the restrained fastener to transform the fastener from a relaxed state to a constrained state; releasing the fastener from the retaining member while the fastener is in the constrained state; advancing the fastener in the constrained state distally within the delivery tool; ejecting the fastener from the delivery tool; and advancing the belt assembly to deliver a second fastener from the belt assembly onto the retaining member.

In accordance with yet another embodiment, a fastener delivery tool is provided that includes a loading chamber for receiving a fastener having a plurality of tines in a relaxed state. The tool also includes a releasable pin or other retaining member for limiting movement of the fastener within the loading chamber. An ejection track is coupled to the loading chamber. A handle is provided that includes a lever, and a tongue and pusher member is coupled to the lever. Movement of the lever advances the tongue to engage the tines so as to transform the fastener from the relaxed state to a constrained state. Movement of the lever also advances the fastener from the loading chamber down the ejection track. A trigger is depressed to eject the fastener from the tool. In one embodiment, the fastener may include overlapping tines in the relaxed state, and the tines may be separated in the constrained state such that, upon release, the tines may be biased to move back towards the related state.

In another embodiment, a method is provided for delivering a fastener using a fastener delivery tool having a fastener therein, the fastener including a pair of tines in a relaxed state. The fastener is secured in the fastener delivery tool using a releasable retaining member. A tongue is advanced in the fastener delivery tool so as to transform the fastener from a relaxed state to a constrained state while the fastener is secured with the releasable retaining member. The retaining member is released and the fastener is advanced in the constrained state distally within the fastener delivery tool using a pusher member. The fastener is ejected from the fastener delivery tool by depressing an actuator.

In still another embodiment, a fastener delivery tool is provided that includes a loading chamber for receiving at least one fastener having a plurality of tines in a relaxed state, the loading chamber including a release pin on which the fastener is loaded. The tool further includes an ejection track communicating with the loading chamber and a lever coupled to a tongue and a pusher member. The tongue is engageable with the plurality of tines of the fastener so as to transform the fastener from the relaxed state to a constrained state. The pusher member is also engageable with a proximal end (e.g., a loop portion) of the fastener so as to translate the fastener to a distal tip of the tool. The fastener is then ejected by depressing a trigger or other actuator.

In still another embodiment, a fastener delivery tool is provided that includes a staging area or section in which a plurality of fasteners are loaded. The fasteners may be loaded individually or within a cartridge. Multiple fasteners may be loaded into the tool, thereby permitting the user to eject or "fire" multiple fasteners successively without having to reload between ejections.

Other aspects and features of the present invention will become apparent from consideration of the following description taken in conjunction with the accompanying drawings.

BRIEF DESCRIPTION OF THE DRAWINGS

As seen in FIG. 4(a), the tines of the fastener are closer together due to advancement of the cartridge retainer and coupled spreader.

FIG. 8(b) is a cross-sectional side view of the fastener delivery tool of FIG. 8(a) taken along line A-A.

FIG. 9(b) is a cross-sectional side view of the fastener delivery tool of FIG. 9(a) taken along line B-B.

FIG. 10(b) is a cross-sectional side view of the fastener delivery tool of FIG. 10(a) taken along line C-C.

FIG. 11(b) is a cross-sectional side view of the fastener delivery tool of FIG. 11(a) taken along line D-D.

FIG. 12(b) is a cross-sectional side view of the fastener delivery tool of FIG. 12(a) taken along line E-E.

FIG. 13(b) is a cross-sectional side view of the fastener delivery tool of FIG. 13(a) taken along line F-F.

FIG. 14(b) is a cross-sectional side view of the fastener delivery tool of FIG. 14(a) taken along line G-G.

DETAILED DESCRIPTION OF THE EXEMPLARY EMBODIMENTS

Figure 1:
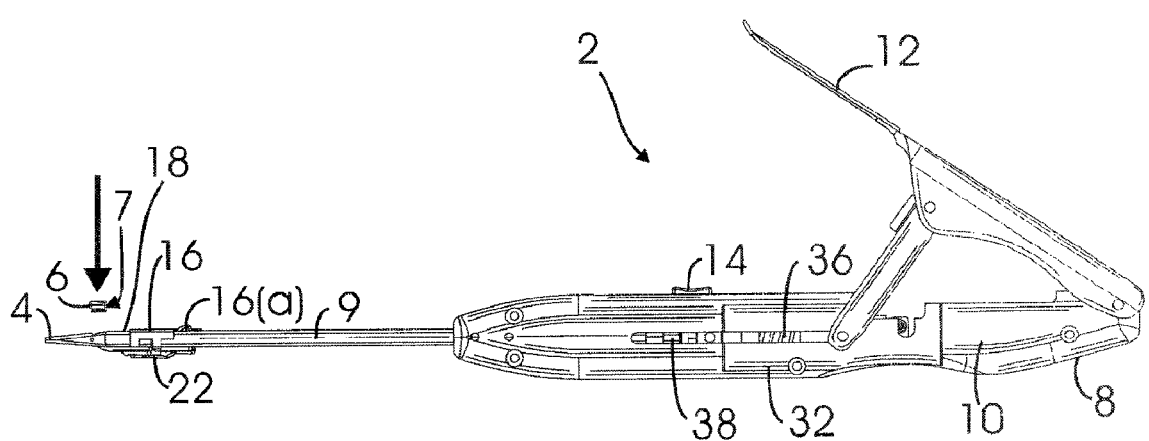
FIG. 1 is a side view of an exemplary embodiment of a fastener delivery tool that includes a cartridge including a fastener being loaded into a loading chamber of the fastener delivery tool.

Turning to the drawings, FIG. 1 shows a first embodiment of a fastener delivery tool 2. The fastener delivery tool 2 includes a distal tip 4 or snout from which one or more fastener(s) 6 (described in more detail below) may be ejected and a proximal end 8 that may be grasped by a user during positioning and/or delivery of the fastener 6. The distal tip 4 and proximal end 8 of the tool 2 are separated by an elongated shaft 9. The fastener 6 may be stored within a cartridge 7 that may be loaded into the fastener delivery tool 2. The fastener delivery tool 2 also includes a proximally located handle 10 having a lever 12 or other actuator that may be used to deploy the fastener(s) 6. The handle 10 may be ergonomically shaped such that a user may easily manipulate the fastener delivery tool 2 into position. The handle 10 preferably includes a spring-biased trigger 14, e.g., a depressible button that may be used to eject the fastener 6 from the distal tip 4 of the tool 2.

A cartridge retainer 16 is provided on the shaft 9 that may be movable along the axial direction of the shaft 9. As described more fully below, the cartridge retainer 16 may be used to retain or otherwise secure the cartridge 7 for subsequent deployment steps of the fastener 6. In addition, the cartridge retainer 16 may transform the fastener 6 into a partially constrained or tensioned state.

Figure 2A:
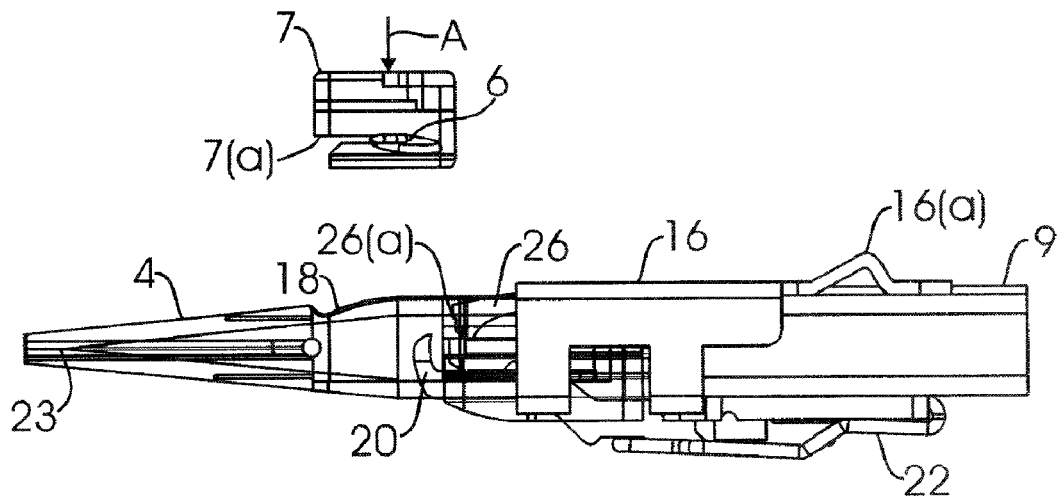
FIG. 2(a) is a cross-sectional side view of a distal tip of the fastener delivery tool shown in FIG. 1, showing the fastener being loaded into the loading chamber (arrow A).
Figure 2B:
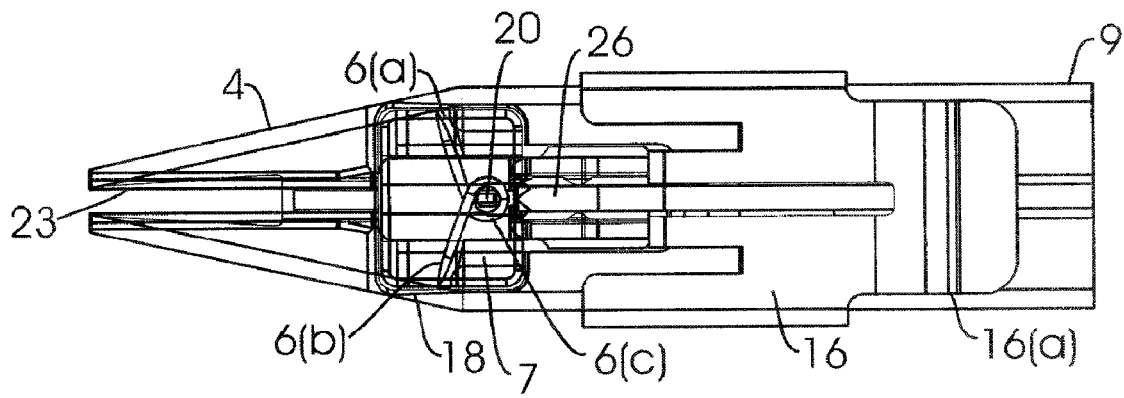
FIG. 2(b) is a cross-sectional top view of the distal tip of the fastener delivery tool shown in FIG. 2(a).

FIGS. 2(*a*) and 2(*b*) illustrate the distal end of the fastener delivery tool 2. As best seen in FIG. 2(*a*), a fastener 6 may be pre-loaded in a cartridge 7, e.g., in a parent or relaxed state. In the relaxed state, the fastener 6 may include a pair of overlapping tines 6(*a*), 6(*b*) (best seen in FIG. 2(*b*)) that may be angled with respect to one another. The fastener 6 further includes a loop portion 6(*c*), e.g., defined by ends of the tines 6(*a*), 6(*b*). In an exemplary embodiment, the fastener 6 may be formed from an elastic or superelastic material, such as a Nickel-Titanium alloy (Nitinol). Additional information on exemplary embodiments of fasteners that may be delivered using the tool 2 are disclosed in application Ser. Nos. 10/681,700, filed Oct. 8, 2003, and 11/004,445, filed Dec. 3, 2004, the entire disclosures of which are expressly incorporated by reference herein.

The fastener 6 may be secured or otherwise retained in a groove 7(*a*) or slot in the cartridge 7. The cartridge 7 containing the fastener 6 may be inserted (in the direction of arrow A in FIG. 2(*a*)) into a loading chamber 18 located at the distal end of the shaft 9. During this loading process, the loop portion 6(*c*) of the fastener 6 may be lowered over a pin or other retaining member 20. The retaining member 20 may be movable between an engaged state (shown in FIG. 2(*b*)) and a disengaged state (described in more detail below). The retaining member 20 may be biased in the engaged state by a spring 22 or other biasing mechanism. The retaining member 20 advantageously secures the fastener 6 within the tool 2 during the process of transforming the fastener 6 from the relaxed, parent state to the constrained state (e.g., a U-shaped configuration).

Still referring to FIGS. 2(*a*) and 2(*b*), the distal tip 4 of the tool 2 includes an ejection track 23. The ejection track 23 is connected to or otherwise communicates with the loading chamber 18. During deployment of the fastener 6, the tines 6(*a*), 6(*b*) may be forced into the U-shaped configuration and the fastener 6 may be advanced from the loading chamber 18 and into the ejection track 23 (described in more detail below).

Figure 3A:
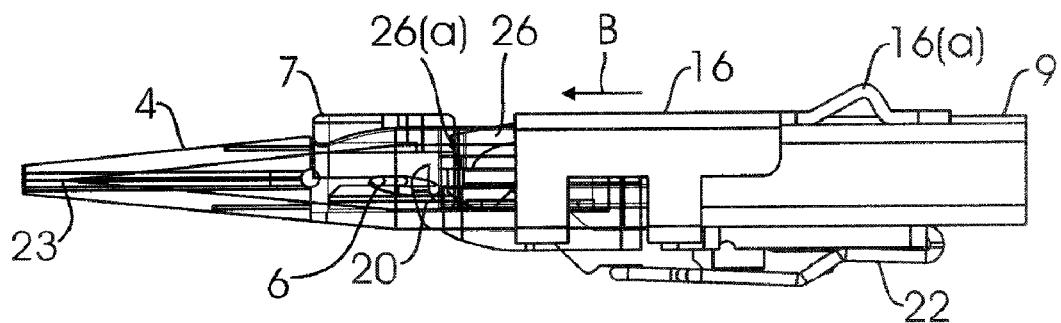
FIG. 3(a) is a cross-sectional side view of the distal tip of the fastener delivery tool shown in FIG. 1, showing initial advancement of the cartridge retainer in the distal direction (arrow B).
Figure 3B:
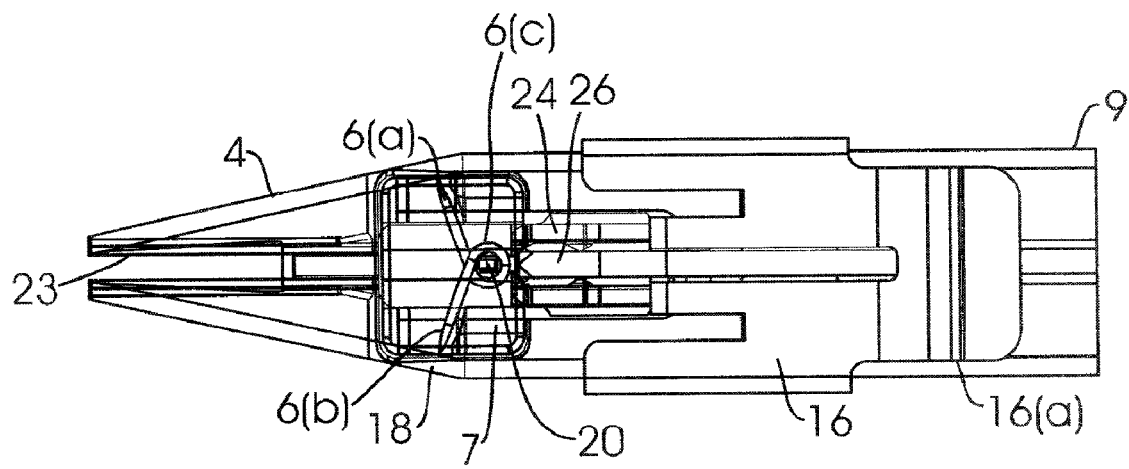
FIG. 3(b) is a cross-sectional top view of the distal tip of the fastener delivery tool shown in FIG. 3(a).
Figure 4A:
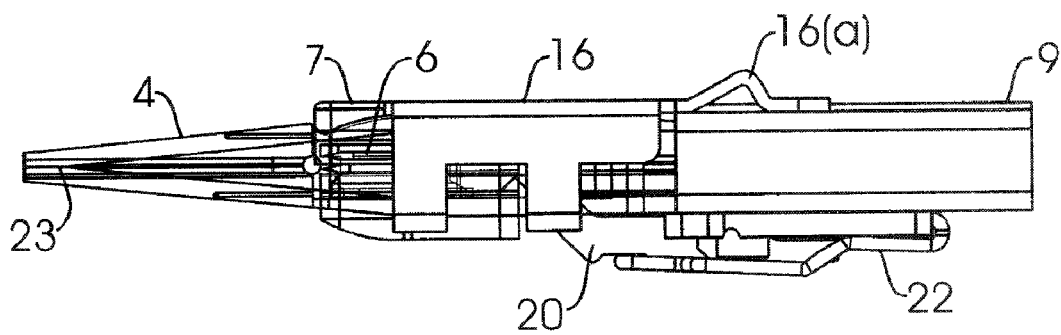
FIG. 4(a) is a cross-sectional side view of the distal tip of the fastener delivery tool shown in FIG. 1, showing complete advancement of the cartridge retainer.
Figure 4B:
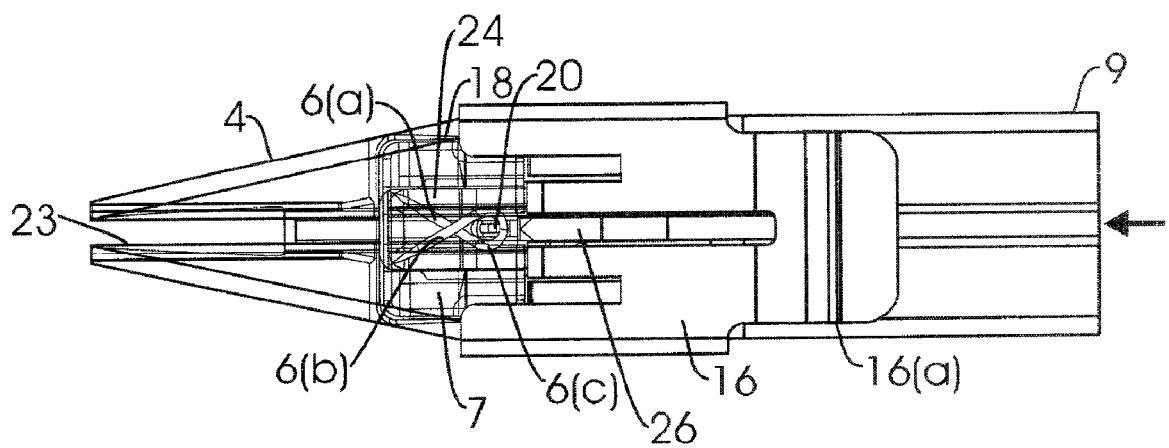
FIG. 4(b) is a cross-sectional top view of the distal tip of the fastener delivery tool shown in FIG. 4(a), showing initial advancement of the tongue in the distal direction.

FIGS. 3(*a*) and 3(*b*) illustrate the next step involved in deploying the fastener 6. As seen in FIGS. 3(*a*) and 3(*b*), the cartridge retainer 16 may be advanced distally (shown by arrow B in FIG. 3(*a*)). In one embodiment, the cartridge retainer 16 may be advanced manually, for example, by depressing a finger on ridge 16(*a*). Alternatively, the cartridge retainer 16 may also be advanced automatically, for example, through movement of the handle 10. The cartridge retainer 16 is coupled to a spreader 24 that may engage the tines 6(*a*), 6(*b*) of the fastener 6. The spreader 24 may include a slot or groove in which the fastener tines 6(*a*), 6(*b*) may be received. Movement of the cartridge retainer 16 from the position shown in FIGS. 3(*a*) and 3(*b*) to the position shown in FIGS. 4(*a*) and 4(*b*) causes the spreader 24 also to move distally. The spreader 24 contacts the tines 6(*a*), 6(*b*) of the fastener 6 and causes the fastener 6 to transform into a partially constrained state (best shown in FIG. 4(*b*).

Figure 5A:
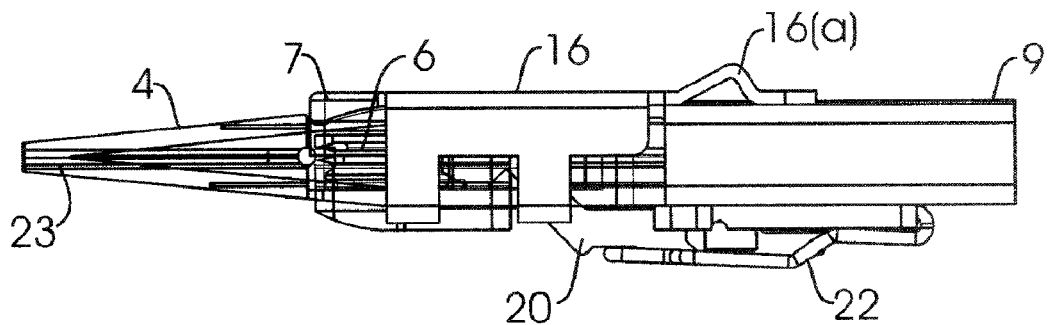
FIG. 5(a) is a cross-sectional side view of the distal tip of the fastener delivery tool shown in FIG. 1, showing a tongue advanced and entering a loop in the fastener.
Figure 5B:
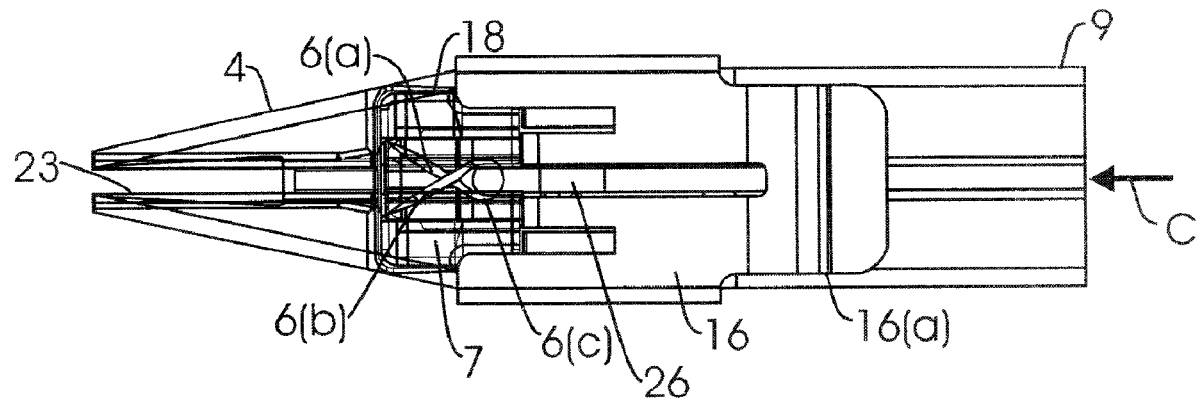
FIG. 5(b) is a cross-sectional top view of the distal tip of the fastener delivery tool shown in FIG. 5(a), showing the tongue entering the loop in the fastener.
Figure 6A:
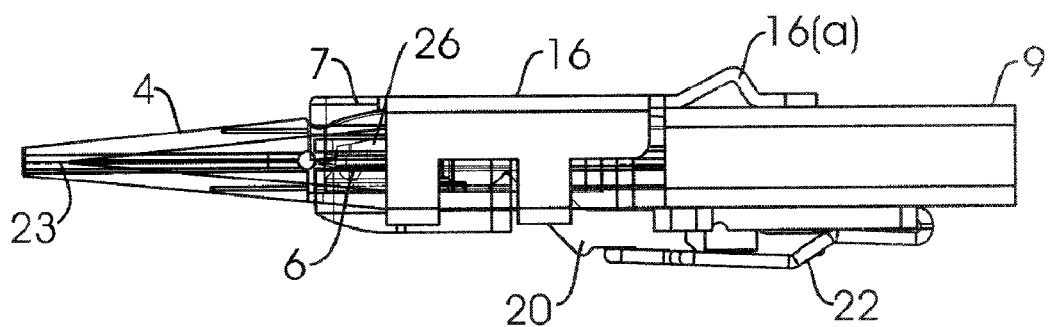
FIG. 6(a) is a cross-sectional side view of the distal tip of the fastener delivery tool shown in FIG. 1, showing transformation of the fastener into a constrained configuration (i.e., a U-shaped configuration). Advancement of the tongue in the distal direction spreads the tines of the fasteners outward to form the U-shaped configuration.
Figure 6B:
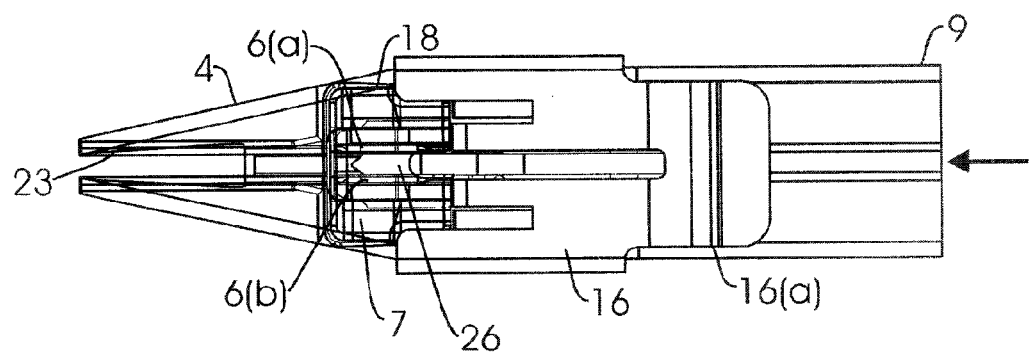
FIG. 6(b) is a cross-sectional top view of the distal tip of the fastener delivery tool shown in FIG. 6(a).

FIGS. 5(*a*) and 5(*b*) illustrate the tongue 26 advancing in the direction of arrow C shown in FIG. 5(*b*). As best seen in FIGS. 2(*a*) and 3(*a*), the tongue 26 includes one or more teeth 26(*a*). The tongue 26 is advanced in the direction of arrow C and the one or more teeth 26(*a*) drop within the loop 6(*c*) of the fastener 6(*c*). FIGS. 5(*a*) and 5(*b*) illustrate the teeth 26(*a*) within the fastener loop 6(*c*). The tongue 26 is advanced further in the distal direction as shown in FIGS. 6(*a*) and 6(*b*) to transform the fastener 6 from the partially constrained state to the fully constrained state (i.e., the U-shaped configuration). The U-shaped configuration is obtained by forcibly parting the tines 6(*a*), 6(*b*) of the fastener 6 using the teeth 26(*a*) of the tongue 26, while restraining the proximal end or loop portion 6(*c*) of the fastener 6, e.g., using retaining member 20.

Figure 7A:
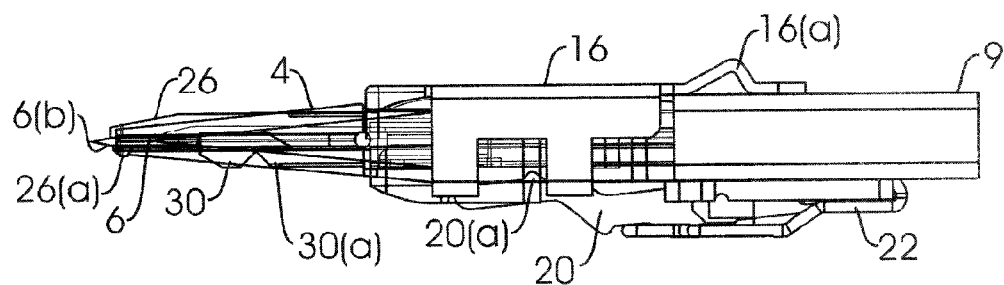
FIG. 7(a) is a cross-sectional side view of the distal tip of the fastener delivery tool shown in FIG. 1, showing translation of the fastener in the distal direction through advancement of a pusher member. The tongue is also translated in the distal direction along with the fastener to aid in maintaining the U-shaped configuration.
Figure 7B:
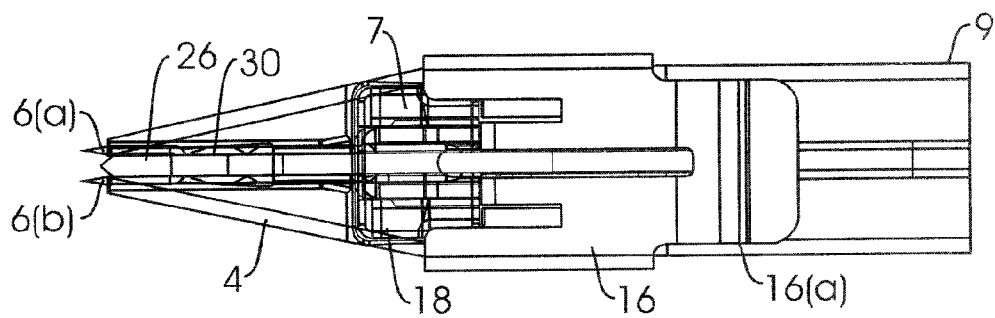
FIG. 7(b) is a cross-sectional top view of the distal tip of the fastener delivery tool shown in FIG. 7(a), showing the tines of the fastener projecting slightly beyond the distal-most end of the fastener delivery tool.

FIGS. 7(*a*) and 7(*b*) illustrate the fastener 6 being advanced through the ejection track 23. After the fastener 6 has assumed the U-shaped configuration, the retaining member 20 may be moved from the engaged state to the disengaged state. FIG. 7(*a*) illustrates the retaining member 20 in the disengaged state. With the retaining member 20 in the disengaged state, the fastener 6 may be free to move distally down the ejection track 23. In one embodiment, the retaining member 20 is moved from the engaged state to the disengaged state by interaction of a cam structure 20(*a*) located on the retaining member 20 with a pusher member 30 (see FIG. 7(*a*)). For example, in the engaged state, the cam structure 20(*a*) on the retaining member 20 may rest within a corresponding groove 30(*a*) in the pusher member 30. When the pusher member 30 is advanced in the distal direction, the cam structure 20(*a*) is forced out of the groove 30(*a*) and forces the retaining member 20 to the disengaged state.

Still referring to FIGS. 7(*a*) and 7(*b*), the pusher member 30 contacts a proximal end of the fastener 6 and pushes or advances the fastener 6 down the ejection track 23. In one embodiment, the pusher member 30 continues to advance the fastener 6 until the fastener 6 reaches a position within the ejection track 23 shown in FIGS. 7(*a*) and 7(*b*). In this position, the fastener 6 is positioned such that the tines 6(*a*), 6(*b*) project slightly from the distal-most end of the tool 2.

This configuration may permit a physician or other user to probe areas of tissue for the optimal insertion location. For example, the physician may probe an area of tissue that may be calcified or plaque-laden and not suitable for placement of a fastener 6. In this regard, the physician may move instead to another more potentially desirable location adjacent the calcified location. Once the desired location is reached, the fastener 6 may be completely ejected from the tool 2, e.g., by depressing the trigger 14 (shown, for example, in FIG. 15(*e*)).

Figure 8A:
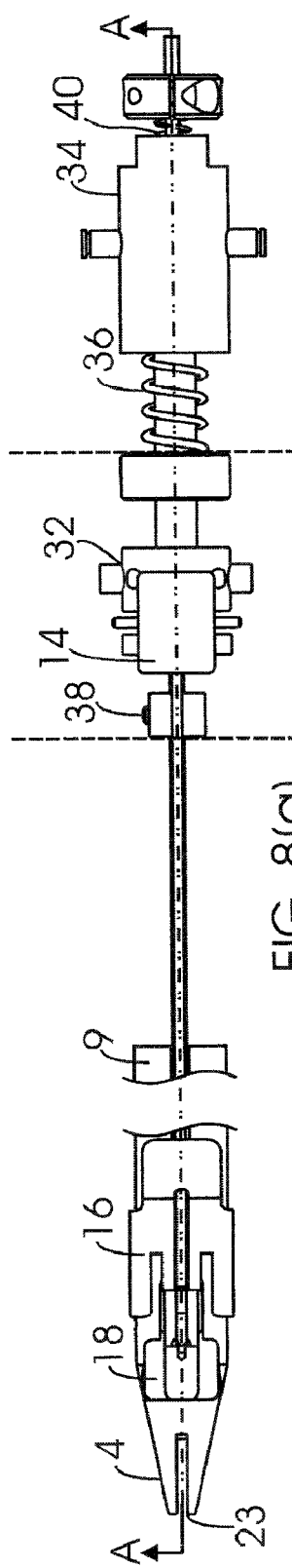
FIG. 8(a) is a partial top down plan view of the fastener delivery tool of FIG. 1 with the handle and lever removed for clarity, and showing the loading chamber empty and ready for receiving a cartridge containing a fastener.
Figure 8A:
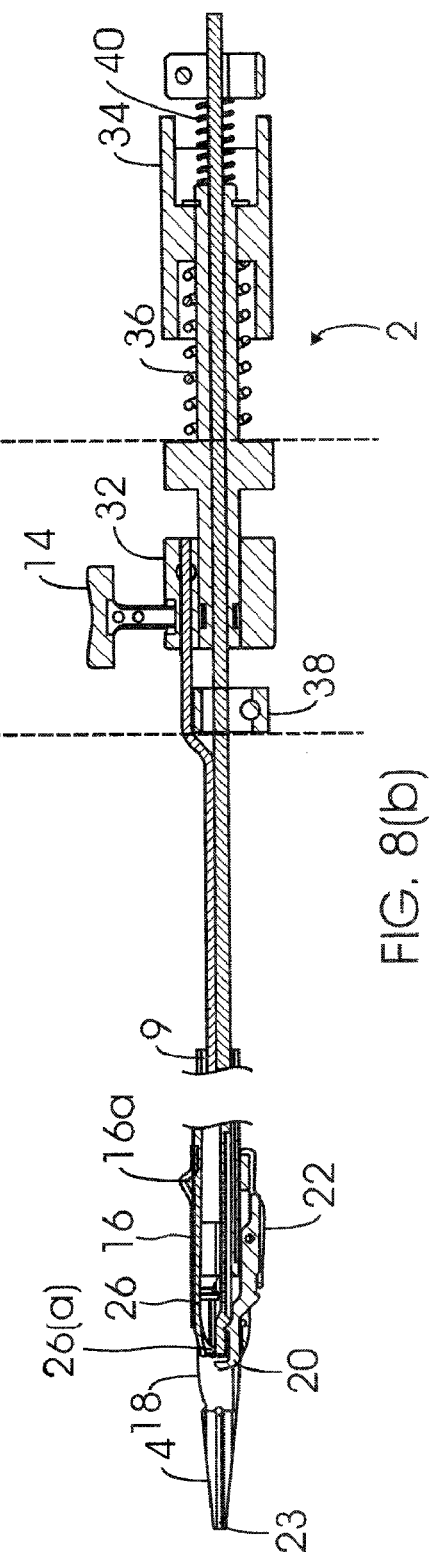
Figure 9A:
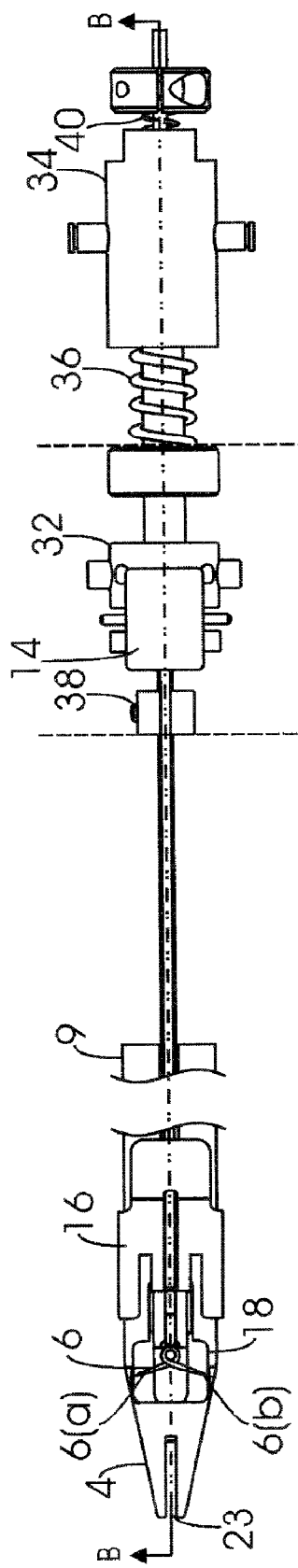
FIG. 9(a) is a partial top down plan view of the fastener delivery tool of FIG. 1 with the handle and lever removed for clarity, and showing a fastener loaded in the loading chamber of the fastener delivery tool.
Figure 9A:
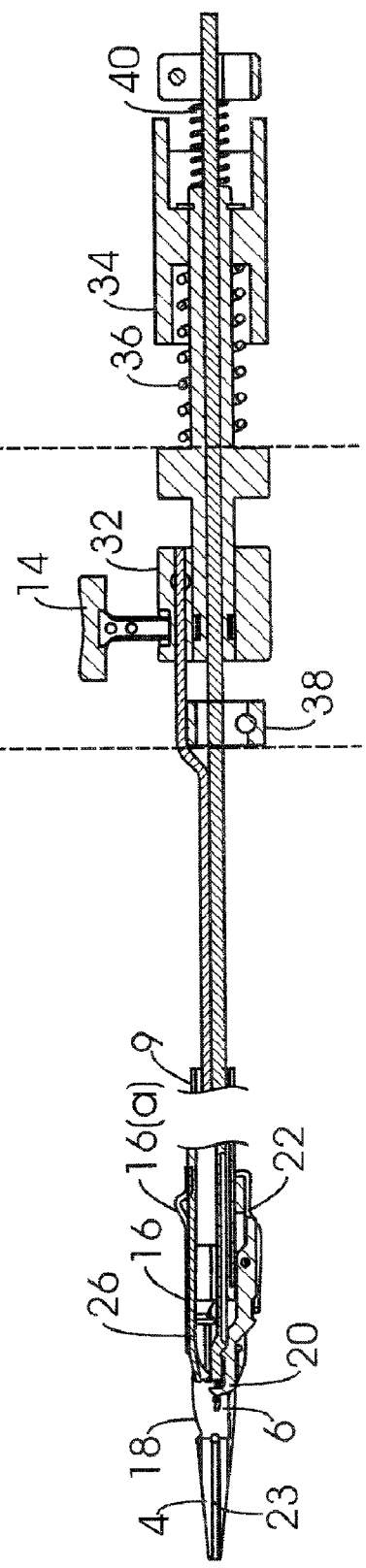
Figure 10A:
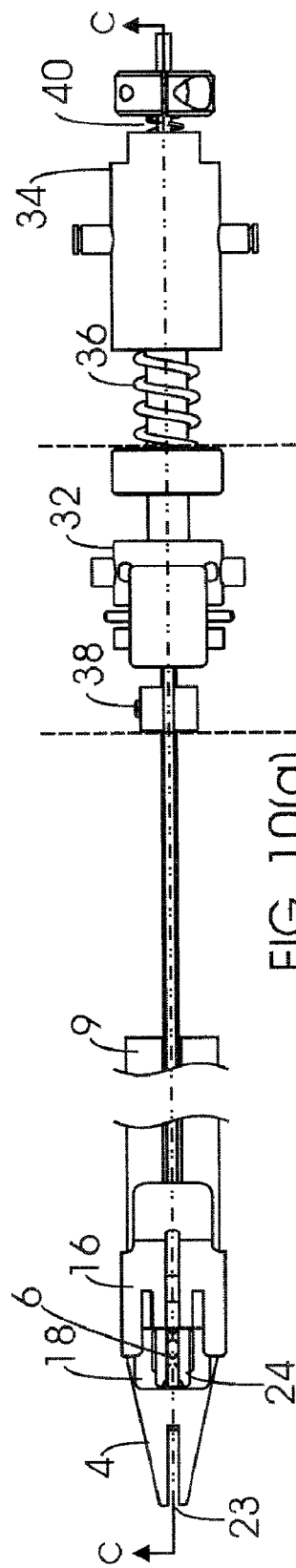
FIG. 10(a) is a partial top down plan view of the fastener delivery tool of FIG. 1 with the handle and lever removed for clarity, and showing the cartridge retainer advanced distally to secure the fastener via a spreader that draws the two tines of the fastener closer to one another.
Figure 10A:
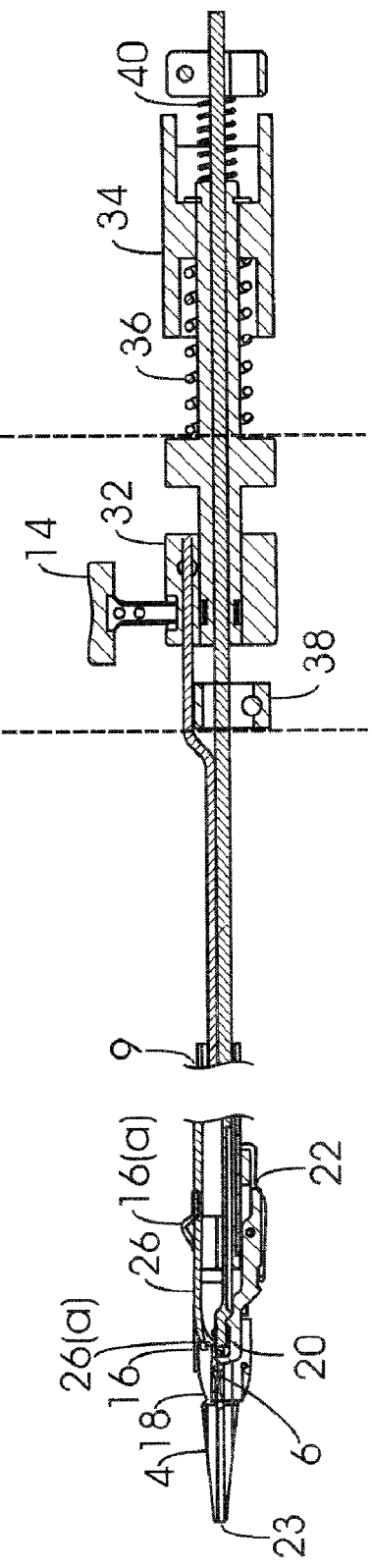

FIGS. 8(*a*) and 8(*b*) illustrate partial top and side views, respectively, of the fastener delivery tool 2 with the handle 10 and lever 12 removed for clarity. In FIGS. 8(*a*) and 8(*b*), the loading chamber 18 of the device is empty and the cartridge retainer 16 is withdrawn in the proximal direction, permitting loading of another cartridge 7 carrying a fastener 6 into the tool 2. FIGS. 9(*a*) and 9(*b*) illustrate a fastener delivery tool 2 loaded with a single fastener 6 (the cartridge 7 is hidden simply for the sake of clarity). As seen in FIG. 9(*a*), the fastener 6 is in the relaxed or parent state. Referring now to FIGS. 10(*a*) and 10(*b*), the cartridge retainer 16 is then advanced distally to partially constrain the fastener 6 within the spreader 24 (shown in FIG. 10(*a*)).

Figure 11A:
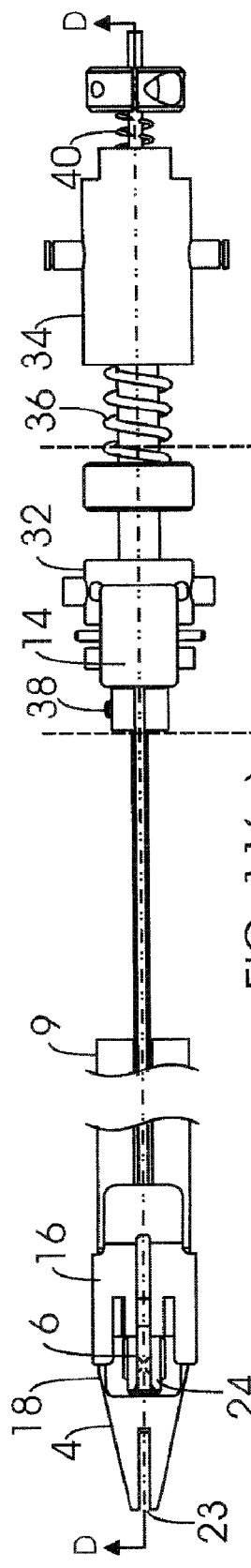
FIG. 11(a) is a partial top down plan view of the fastener delivery tool of FIG. 1 with the handle and lever removed for clarity, and showing the tongue advanced distally to drop into a loop portion of the fastener.
Figure 11A:
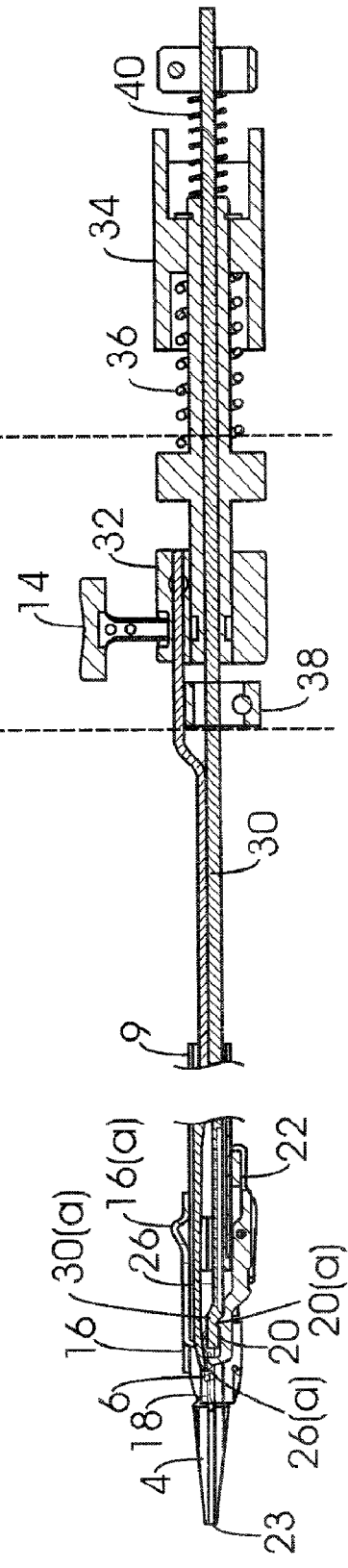

With reference to FIGS. 11(*a*) and 11(*b*), additional depression of the lever 12 on the handle 10 advances the tongue 26 such that the teeth 26(*a*) drop into the loop portion 6(*c*) of the fastener (shown best in FIG. 11(*b*)). The tongue 26 is fixedly coupled to a trigger assembly 32 that may be translated distally as the lever 12 on the handle is depressed. The trigger assembly 32 is biased against an advancement mechanism 34 coupled to the actuating lever 12. Actuation of the lever 12 causes the advancement mechanism 34 to displace distally. This distal displacement is translated to the trigger assembly 32 via a spring 36. The spring 36 may be substantially stiff such that it acts as a rigid linkage between the advancement mechanism 34 and trigger assembly 32 before the compression stage (discussed in detail below). Translation of the advancement mechanism 34 and trigger assembly 32 (and coupled tongue 26) before the compression stage may be best seen in FIGS. 11(a), 11(b), 12(a), and 12(b).

Figure 12A:
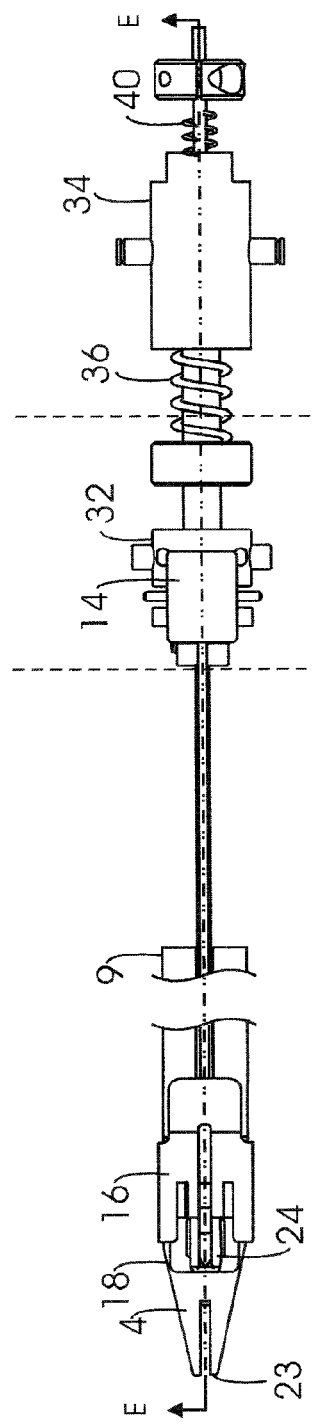
FIG. 12(a) is a partial top down plan view of the fastener delivery tool of FIG. 1 with the handle and lever removed for clarity, and showing additional distal displacement of the tongue to transform the fastener into the U-shaped configuration.
Figure 12A:
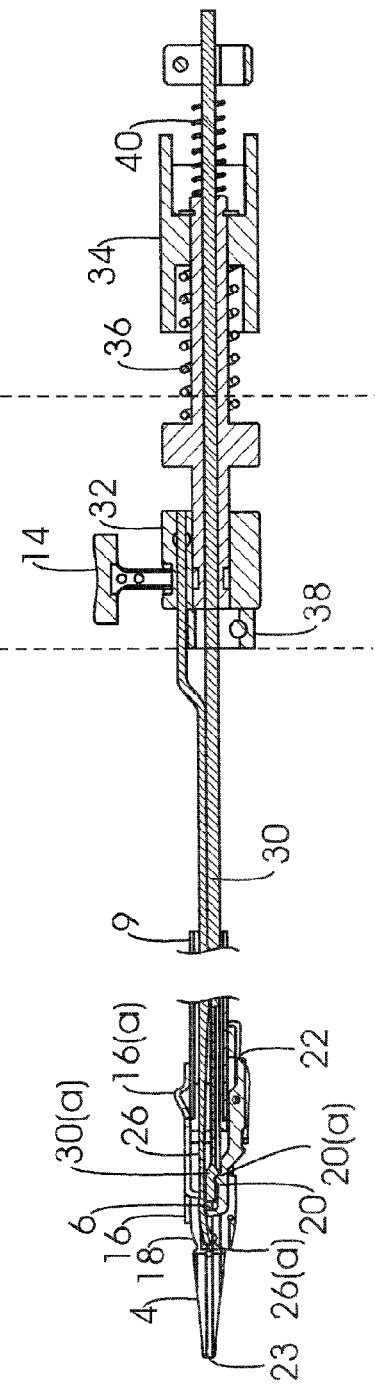

Referring now to FIGS. 12(a) and 12(b), the fastener 6 is then transformed into the fully constrained state (i.e., U-shaped configuration) by advancing the tongue 26 distally, e.g., by partially depressing the handle 10 of the tool 2. The teeth 26(a) of the tongue 26 may advance between the tines 6(a), 6(b) of the fastener 6 to direct the fastener 6 into the U-shaped configuration. At this stage, the fastener 6 may still be retained by retaining member 20.

Figure 13A:
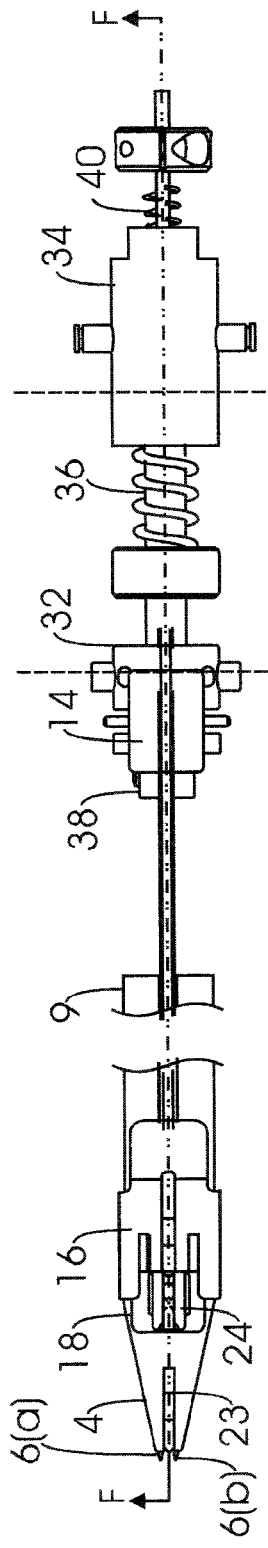
FIG. 13(a) is a partial top down plan view of the fastener delivery tool of FIG. 1 with the handle and lever removed for clarity, and showing the fastener advanced distally such that the two tines project slightly beyond the distal-most edge of the ejection track of the fastener delivery tool.
Figure 13A:
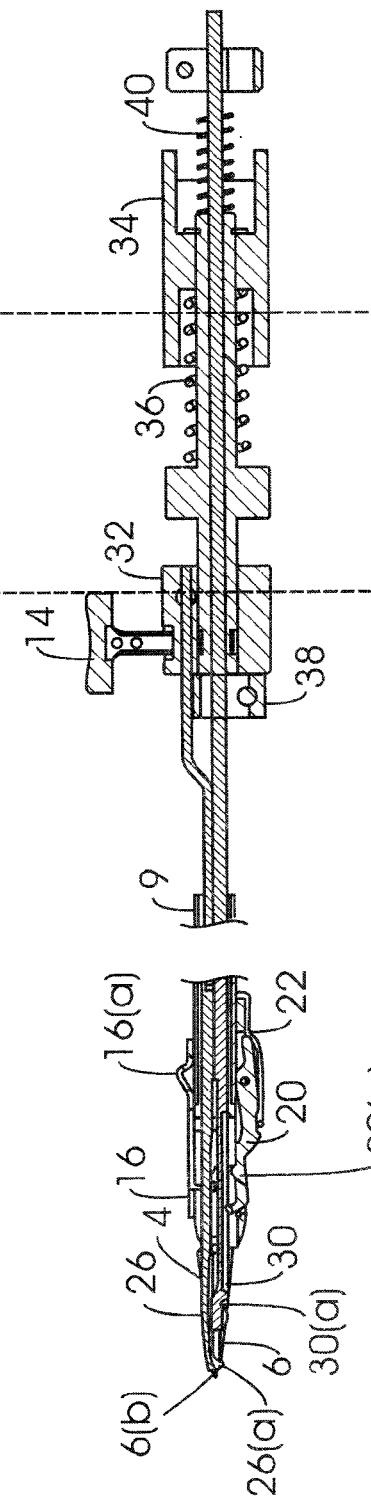

FIGS. 13(a) and 13(b) illustrate the trigger assembly 32 abutting and pushing against a clamp 38 that is fixedly coupled to the pusher member 30. Movement of the clamp 38 distally causes corresponding distal movement of the pusher member 30 within the tool 2. The pusher member 30 then advances distally such that the cam 20(a) on the retaining member 20 exits the groove 30(a) in the pusher member, thereby moving the retaining member 20 to the disengaged position. Additional advancement of the handle 12 pushes the fastener 6 down the ejection track 23 of the tool. During this phase of deployment, both the tongue 26 and pusher member 30 move distally in unison. Advancement of the fastener 6 may stop when the tines 6(a), 6(b) project just beyond the distal-most end of the tool 2 (as shown in FIGS. 13(a) and 13(b).

Figure 14A:
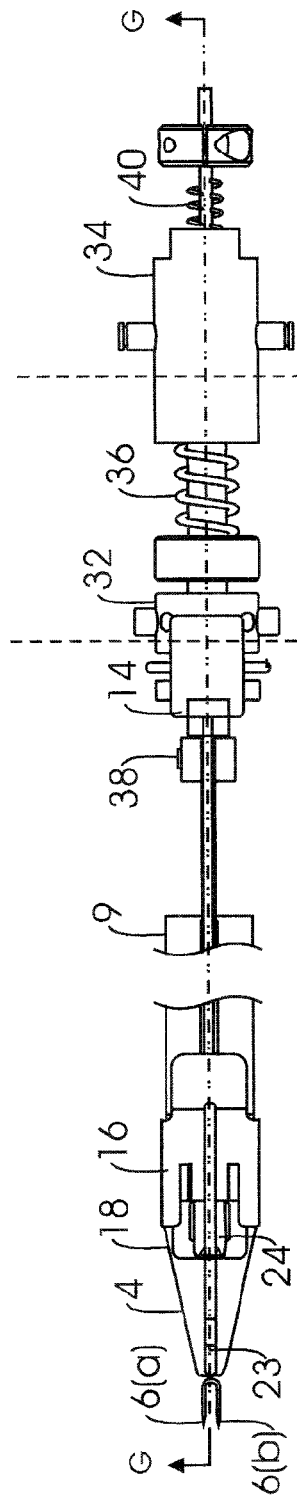
FIG. 14(a) is a partial top down plan view of the fastener delivery tool of FIG. 1 with the handle and lever removed for clarity, and showing the ejection of the fastener from the ejection track of the fastener delivery tool in the U-shaped configuration.
Figure 14A:
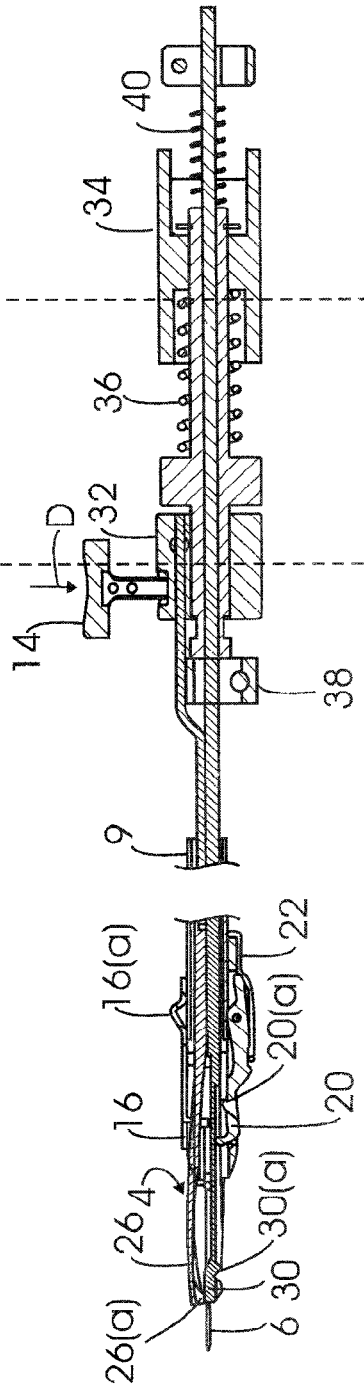

FIGS. 14(a) and 14(b) illustrate ejection of the fastener 6 from the tool 2. After the spring 36 has been fully compressed and the actuating lever 12 is in the position shown in FIG. 15(e), depression of the trigger 14 (illustrated by arrow D in FIG. 14(b)) causes the pusher member 30 to move rapidly in the distal direction to eject the fastener 6 completely from the ejection track 23. As best seen in FIG. 14(a), the fastener 6 may be ejected in the U-shaped configuration into the adjacent tissue (not shown).

As seen in FIGS. 8 through 14, the tool 2 may also include a proximally located restoring spring 40 to aid in restoring the mechanical linkages (e.g., tongue 26, pusher member 30 and associated trigger assembly 32 and advancement mechanism 34) after the fastener 6 has been ejected from the tool 2.

Figure 15A:
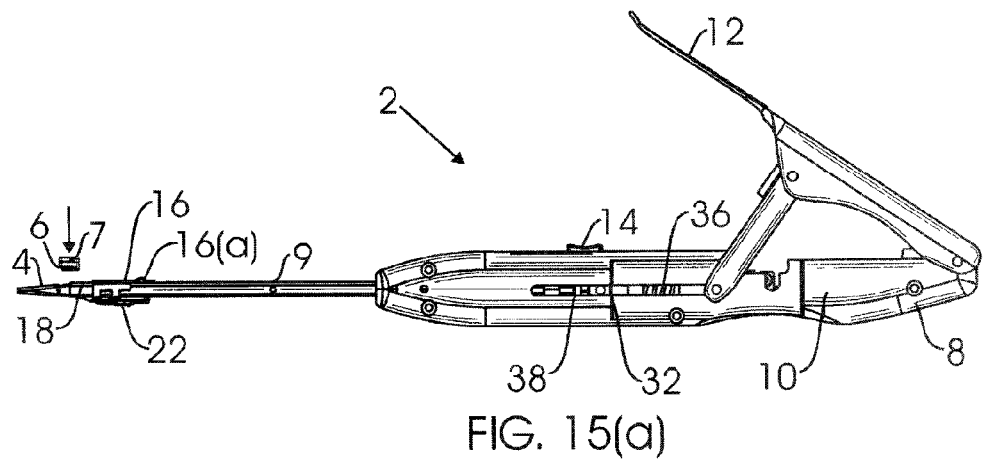
FIG. 15(a) is a side view of an embodiment of a fastener delivery tool, showing a cartridge being loaded into the loading chamber of the device.
Figure 15B:
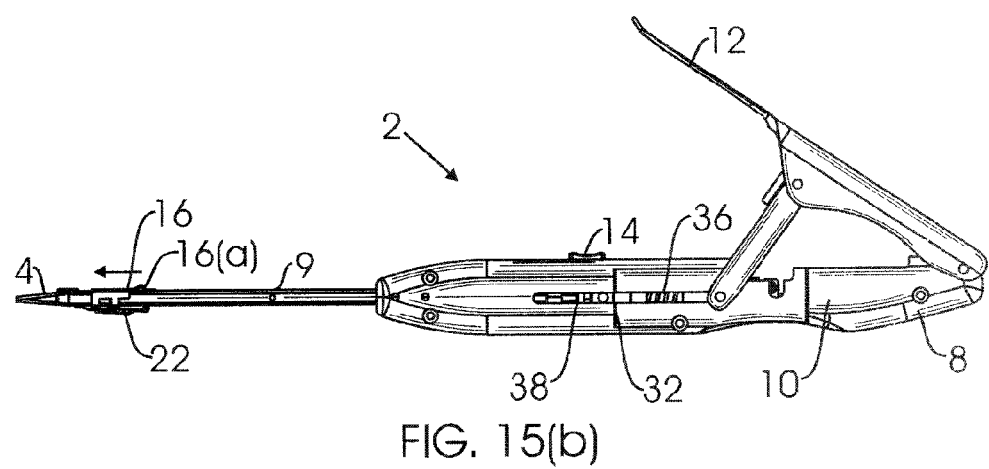
FIG. 15(b) is a side view of the fastener delivery tool shown in FIG. 15(a), showing the cartridge retainer being advanced in the distal direction (see arrow in FIG. 15(b)) over the cartridge.
Figure 15C:
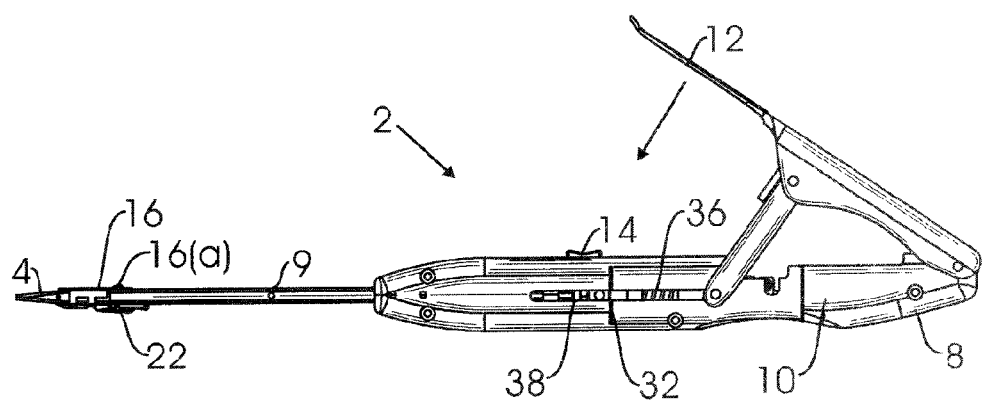
FIG. 15(c) is a side view of the fastener delivery tool shown in FIG. 15(a), showing the fastener being transferred from the cartridge to the distal tip of the fastener delivery tool by actuation of the lever.

FIGS. 15(a) through 15(e) illustrate the various stages of an exemplary method that may be used to deliver a fastener 6 using the fastener delivery tool 2. FIG. 15(a) illustrates a cartridge 7 carrying a fastener 6 being loaded into the loading chamber 18 of the tool 2. FIG. 15(b) illustrates the cartridge retainer 16 being moved distally (in the direction of the arrow in FIG. 15(b)). This movement of the cartridge retainer 16 advances the spreader 24 (not shown in FIG. 15) to place the fastener 6 in a partially constrained state. FIG. 15(c) shows the handle 10 being depressed partially. At this stage, the teeth 26(a) of the tongue 26 drop into the loop portion of the fastener 6 and advance further distally to transform the fastener 6 into the U-shaped configuration, as described above. Additional movement of the handle 10 transfers the fastener 6 from the loading chamber 18 to the ejection track 23 in the distal tip 4 of the tool 2.

Figure 15D:
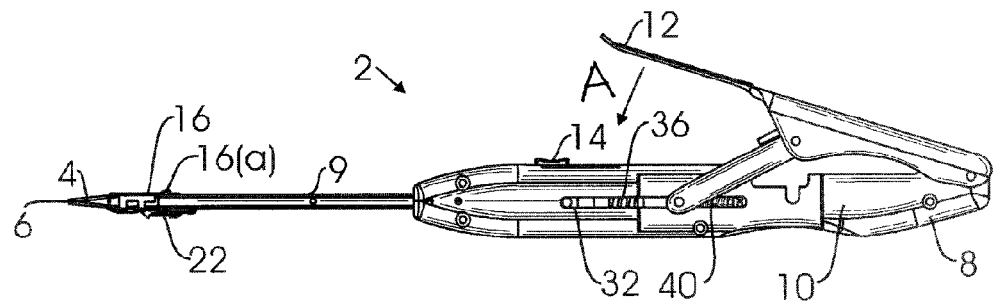
FIG. 15(d) is a side view of the fastener delivery tool shown in FIG. 15(a), showing compression of the ejection spring by additional actuation of the lever.
Figure 15E:
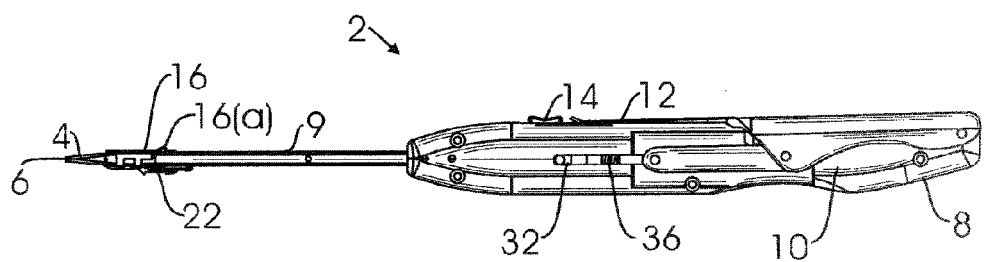
FIG. 15(e) is a side view of the fastener delivery tool shown in FIG. 15(a), showing the fastener delivery tool being fully loaded and ready to deploy the fastener.

FIG. 15(d) illustrates the compression or load-driving step whereby movement of the actuating lever 12 in the direction of the arrow A shown in FIG. 15(d) causes compression of spring 36, also as described above. FIG. 15(e) illustrates the tool 2 in the fully loaded state. The fastener 6 is disposed at the distal tip 4 of the tool 2 with the tines 6(a), 6(b) projecting distally from the ejection track 23. The spring-loaded trigger 14 is then depressed to eject the fastener 6 completely from the tool 2.

Figure 16A:
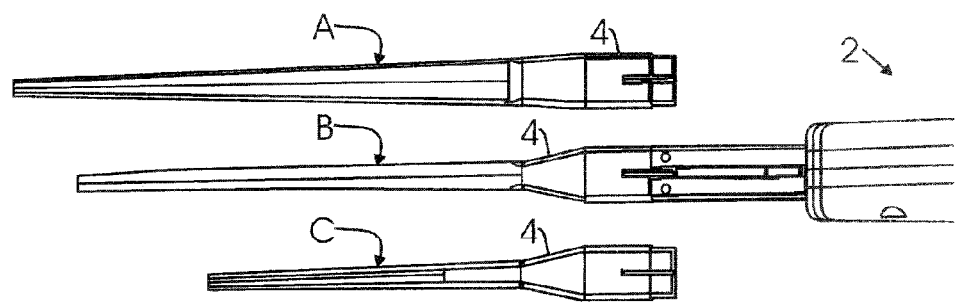
FIGS. 16(a) and 16(b) are top and side views, respectively, showing exemplary configurations for an elongated distal tip for a fastener delivery tool.
Figure 16B:
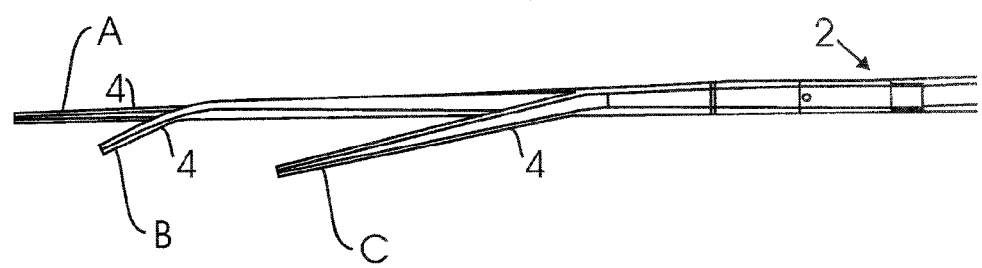

FIGS. 16(a) and 16(b) illustrate alternative configurations, A, B, and C, for an elongated distal tip or snout 4 of the tool 2. The tool 2 may include distal tips 4 of varying lengths in order to facilitate the delivery process. For example, the tips 4 may have lengths between about ten and four hundred millimeters (10-400 mm), or between about five and fifty millimeters (5-50 mm).

The tips 4 may be integrally formed with the tool 2. Alternatively, the tips 4 may be removable and/or interchangeable. In this alternative, the tips 4 and/or tool 2 may include one or more detents or other connectors (not shown) for removably attaching an individual tip 4 to the tool 2. In addition, as best seen in FIG. 16(b), the elongated distal tip or snout 4 may include a variety of geometries or side-profiles, e.g., bends or curves, to increase a user's field of view and/or otherwise facilitate delivering a fastener. Thus, a tip 4 and/or tool 2 may be selected given the particular anatomical presentations encountered during a procedure.

For example, tip A shown in FIG. 16(b) illustrates a configuration in which the elongated distal tip 4 has a substantially straight or flat profile. Tip B illustrates another configuration in which an intermediate portion of the distal tip 4 is bent or curved out of the plane of the tool 2. The bent or curved configuration may be particularly helpful in delivering the fastener 6 generally normal or perpendicular to the surface of the surrounding tissue 90. Tip C illustrates another configuration in which the distal tip 4 is angled with respect to the longitudinal direction of the tool 2.

Figure 17A:
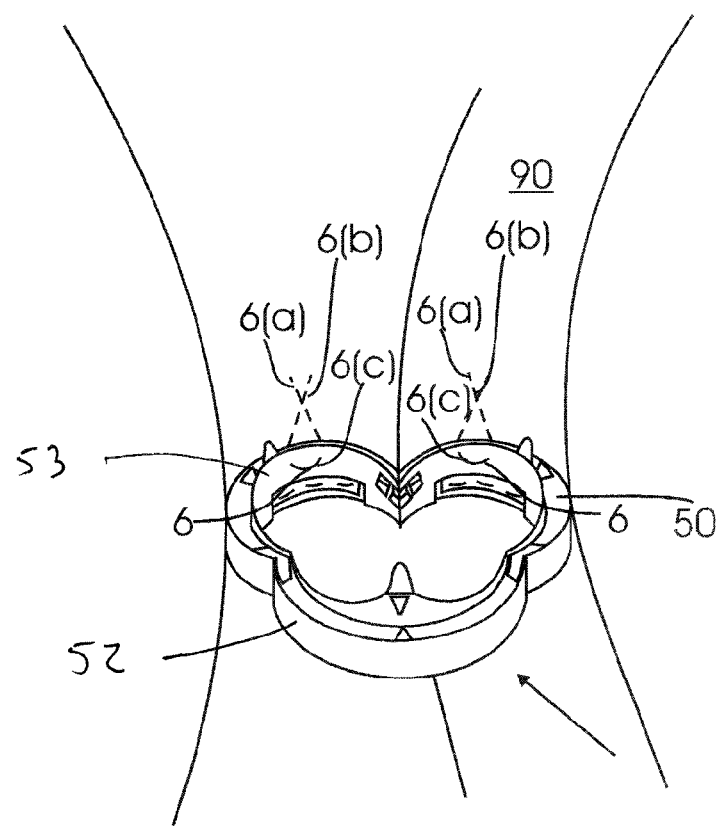
FIG. 17(a) is a cross-sectional view of a patient's body, showing a prosthetic valve secured within a tissue annulus by exemplary fasteners.
Figure 17B:
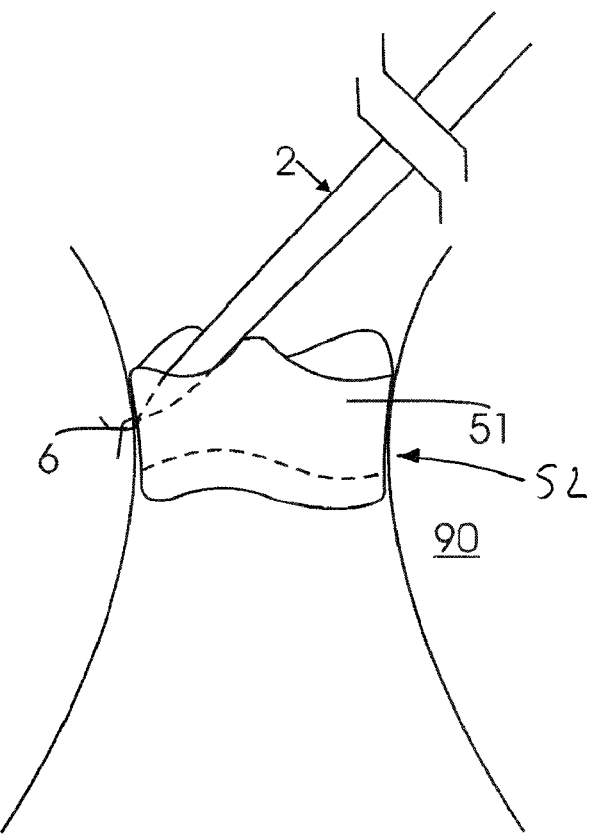
FIG. 17(b) is a cross-sectional view of a patient's body, showing a fastener delivery tool delivering a fastener through a portion of a prosthetic valve into the surrounding tissue.
Figure 17C:
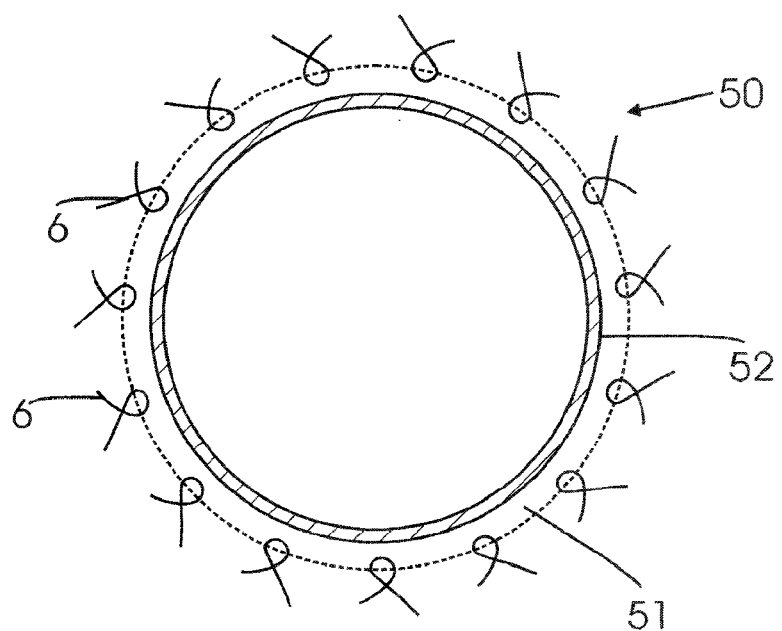
FIG. 17(c) is a radiograph showing a plurality of fasteners deployed about the circumference of a prosthetic valve.

Turning to FIGS. 17(a)-17(c), tool 2, which may be any of the embodiments described herein, may be used to deliver one or more fasteners 6, e.g., during a heart valve replacement procedure. For example, the tool 2 may be used to deliver a plurality of fasteners 6 through a sewing cuff or ring 51 (see FIG. 17*(b)) and/or other component of a prosthetic heart valve assembly 50 into surrounding tissue. Alternatively, it will be appreciated that the tool 2 may be used to deliver one or more fasteners 6, e.g., to secure other devices to tissue or to another device, or to secure tissue structures together.

As shown in FIG. 17(a), the prosthetic valve 50 may be a multiple component prosthesis, e.g., including a gasket member 52, which may include a sewing cuff 51, and a valve member or "crown" 53, including a frame and a plurality of leaflets (not shown for simplicity). Exemplary embodiments of single or multiple component prosthetic heart valve assemblies that may be implanted and/or otherwise attached using the tool 2 are disclosed in U.S. Pat. No. 6,371,983 and in U.S. Publication Nos. 2004/0122516, filed as Ser. No. 10/327,821, 2005/0043760, filed as Ser. No. 10/646,639, 2005/0165479, filed as Ser. No. 10/765,725, 2006/0195184, filed as Ser. No. 11/069,081, 2007/0016285, filed as Ser. No. 11/420,720, 2007/0260305, filed as Ser. No. 11/742,390, and 2008/0033543, filed as Ser. No. 11,742,424. The entire disclosures of these references are expressly incorporated by reference herein.

Initially, the gasket member 52 may be advanced into a biological annulus 90, e.g., using a separate tool (not shown), and maintained at a desired location, e.g., at a site from which native valve leaflets have been removed. The distal tip 4 of the tool 2 (loaded with a fastener 6) may be placed against the sewing cuff 51 with the tip 4 substantially perpendicular to the sewing cuff 51. The tool 2 may be actuated, e.g., by activating the lever 12 and/or trigger 14, to deliver the fastener 6 through the sewing cuff 51 into the underlying tissue. Once the fastener 6 is ejected from the distal tip 4, the tines of the fastener 6 may at least partially recross within the tissue, thereby capturing a portion of the sewing cuff 51 and the underlying tissue within the loop of the fastener 6. A plurality of fasteners 6 may be successively delivered about a circumference of the sewing cuff 51 to affix the prosthetic valve 50 to the surrounding tissue 90.

FIG. 17(a) illustrates two exemplary fasteners 6 in the fully deployed state. As shown in FIG. 17(a), after penetrating the sewing cuff 51 and underlying tissue, the fasteners 6 may be biased to revert towards the parent or unconstrained state (in which the tines of the fasteners 6 at least partially overlap). In this regard, the prosthetic valve 50 may be fixedly secured to the surrounding tissue 90.

FIG. 17(c) illustrates an exemplary image or "radiograph" from a radiography device (not shown), illustrating a plurality of fasteners 6 deployed about the circumference of the prosthetic valve 50. The fasteners 6 and a portion of the gasket member 52 are at least partially radiopaque, and may be seen on a radiograph, while the sewing cuff 51 (shown in phantom in FIG. 17(c)) may be substantially radiolucent, and therefore not visible on the radiograph.

Optionally, the fasteners 6 may be removable from tissue 90 and/or prosthetic valve 50, e.g., if it is desired to remove the valve 50 or relocate a particular fastener. For example, a pliers-like tool (not shown) may be used to remove a fastener after ejection of the fastener 6 from the tool 2, e.g., if the fastener 6 is oriented incorrectly or the fastener 6 does not penetrate deeply enough into the tissue 90. The physician may grasp the loop portion 6(c) of the fastener 6, which may remain at least partially exposed, using the pliers-like tool. The fastener 6 may then be pulled or otherwise retracted proximally to remove the tines of the fastener 6 from the delivery site. Optionally, the tool may be rotated to at least partially open the tines of the fastener 6 to facilitate removal. A replacement fastener 6 may be loaded into the tool 2 and/or otherwise delivered to the delivery site, similar to the methods described above.

Figure 18:
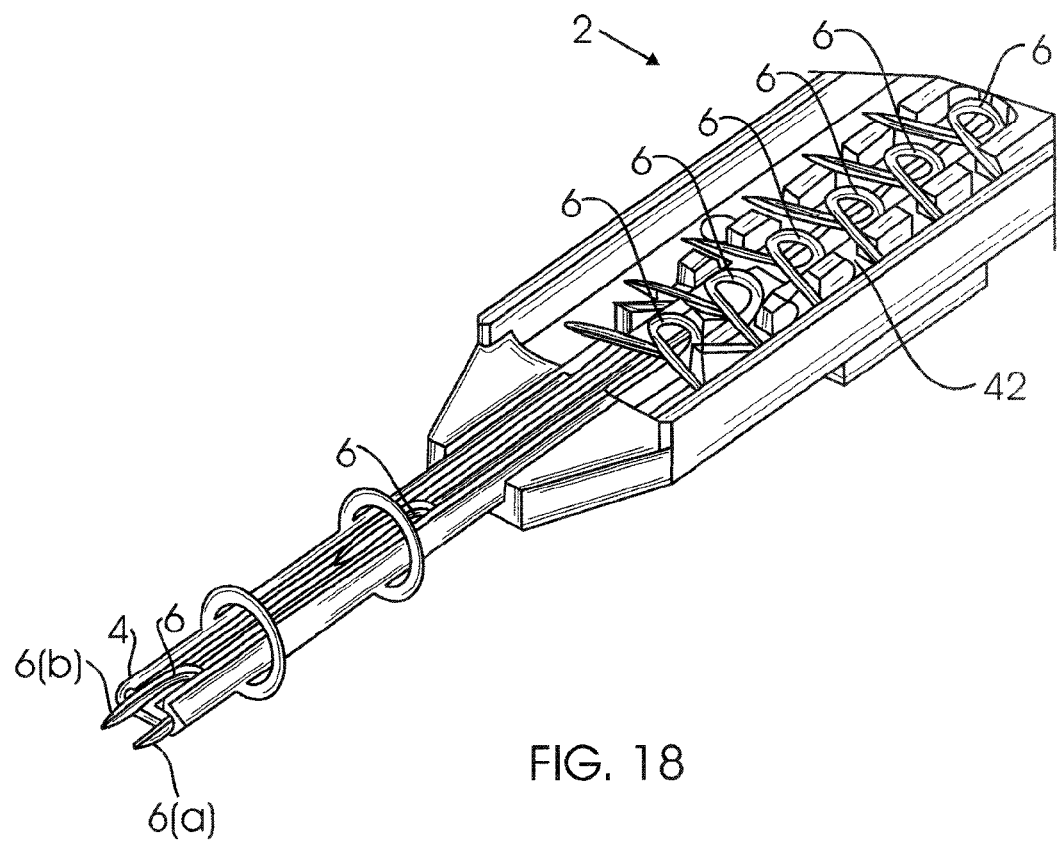
FIG. 18 is an alternative embodiment of a fastener delivery tool that houses a plurality of fasteners.

In an alternative embodiment, a tool may be provided that may accommodate loading multiple fasteners 6 into the tool 2 simultaneously or successively before delivery. Such a tool 2 may be desirable because the tool 2 does not have to be removed from the body cavity to load successive fasteners 6, which may accelerate delivery of the fasteners 6. FIG. 18 illustrates an embodiment of a tool 2, showing a plurality of fasteners 6 loaded into a staging area or section 42. The fasteners 6 may be advanced successively in the distal direction toward the distal tip 4 of the tool 2. A cartridge (not shown) may be provided that holds a plurality of fasteners 6 such that the tool 2 may be loaded with multiple fasteners 6 simply by loading a single cartridge into the tool 2.

Figure 19A:
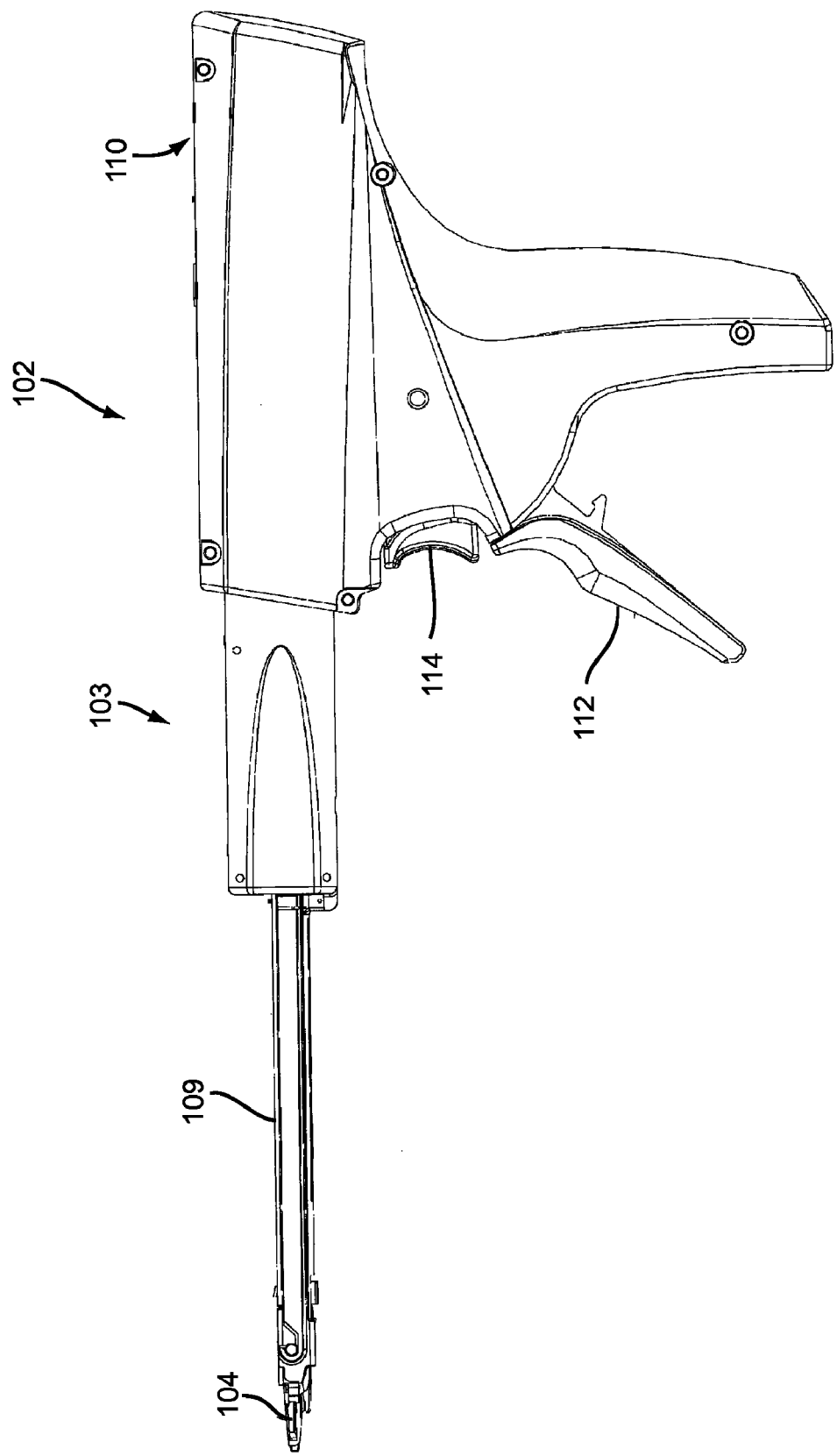
FIGS. 19(a) and 19(b) are side views of another embodiment of a fastener delivery tool, showing a lever on a handle on the tool in unloaded and loaded positions, respectively.
Figure 19B:
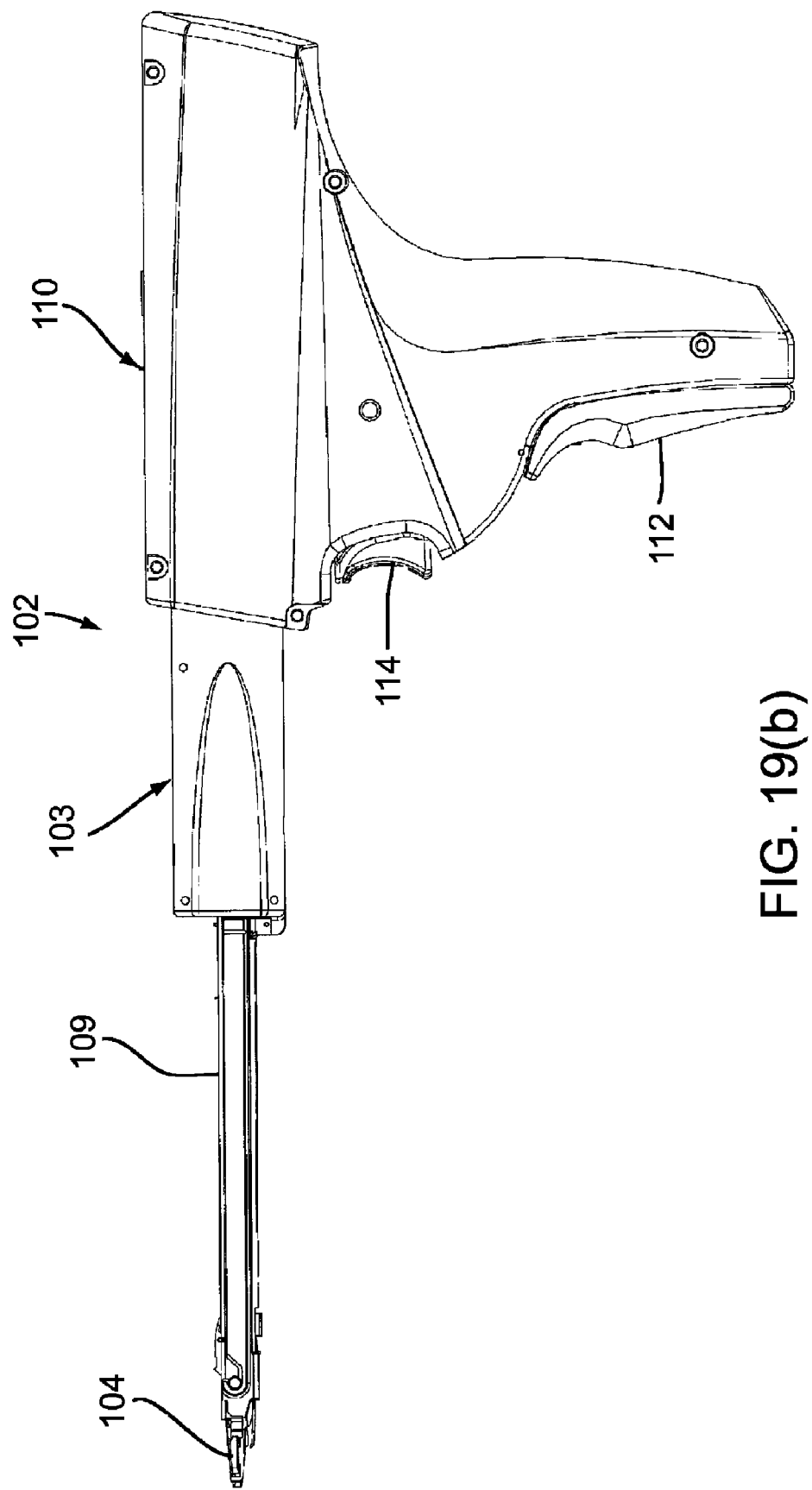
Figure 20A:
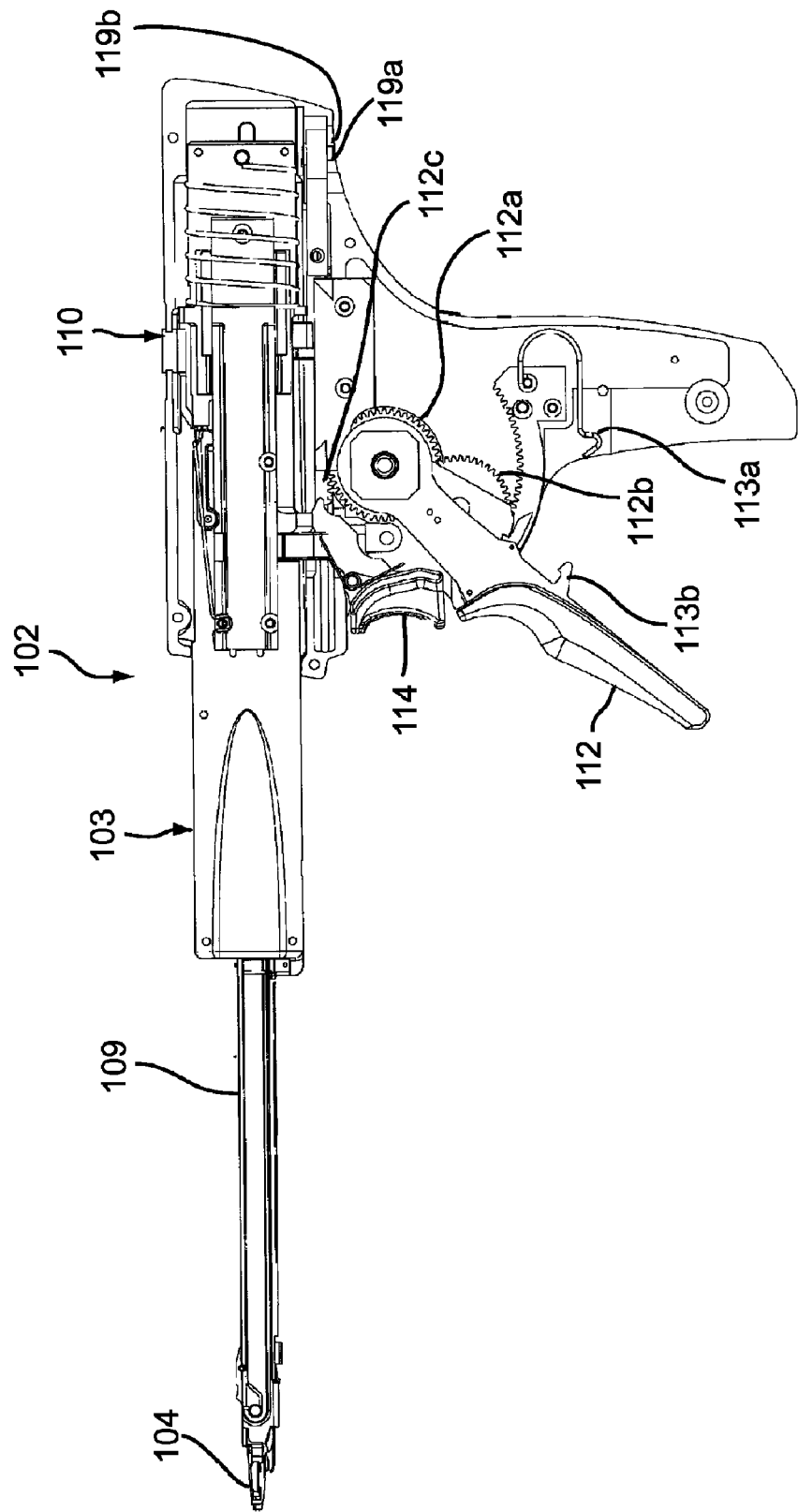
FIGS. 20(a) and 20(b) are side views of the tool of FIGS. 19(a) and 19(b), respectively, with a cover removed to show internal components of the handle.
Figure 20B:
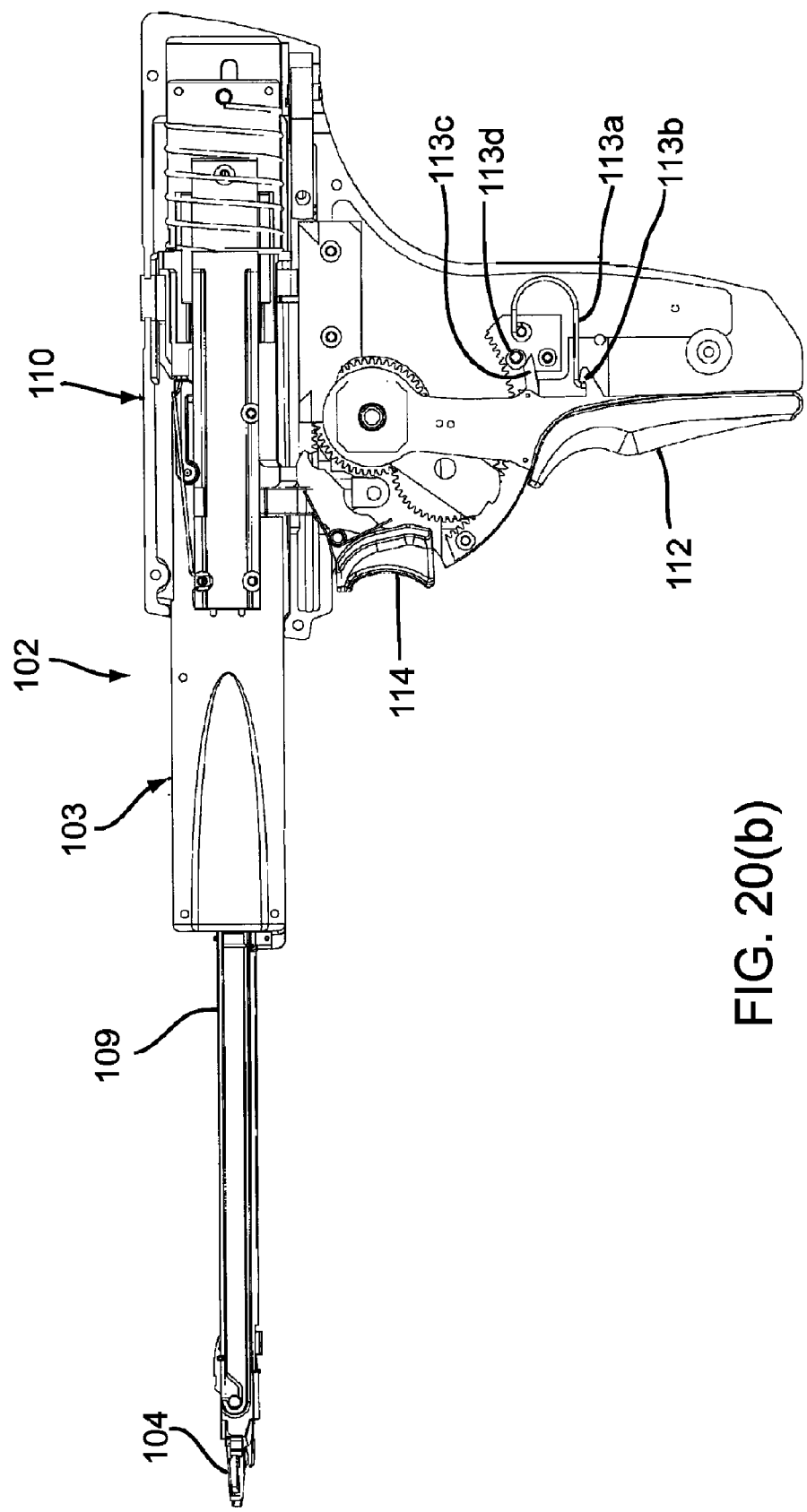
Figure 21A:
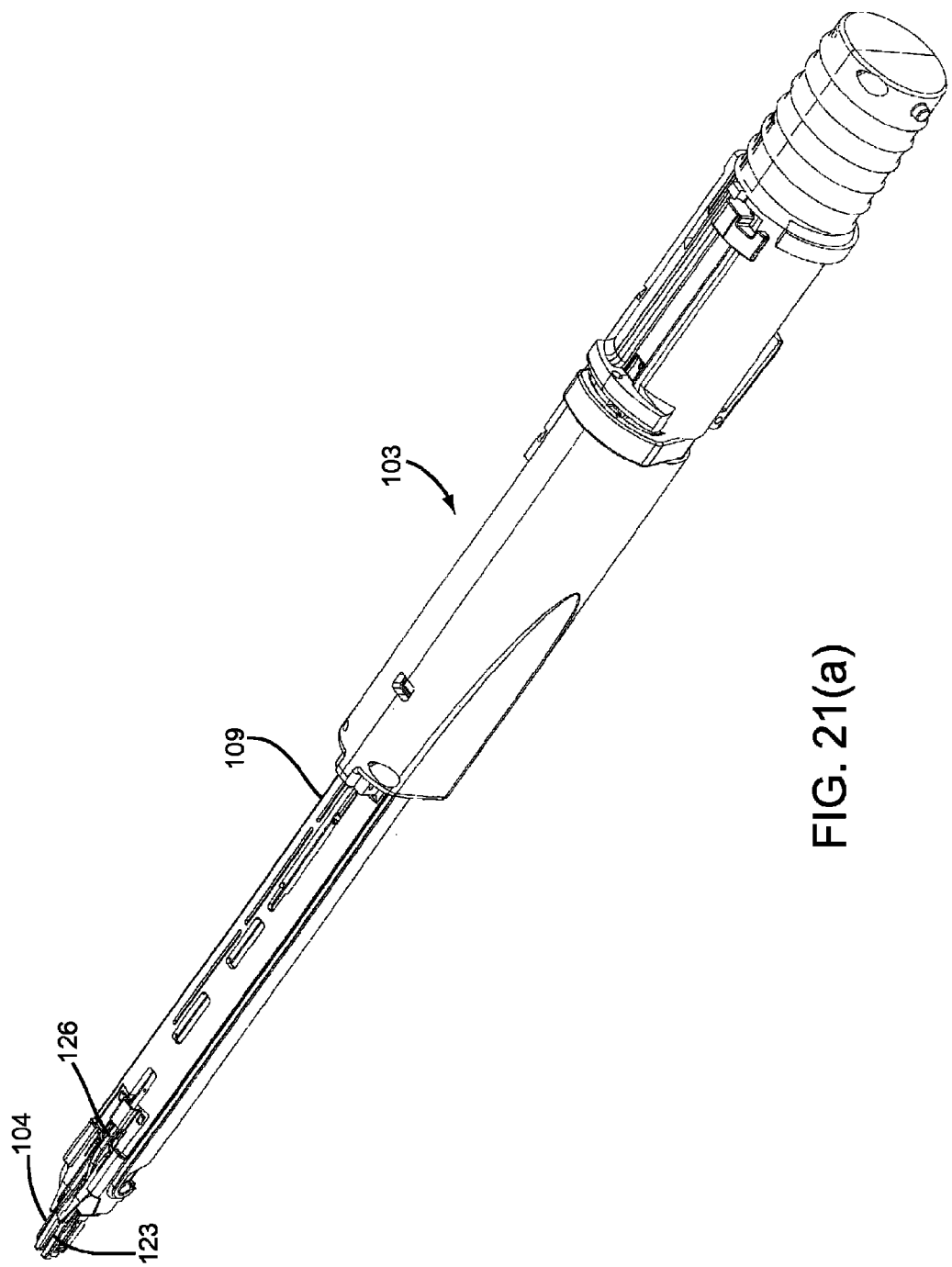
FIG. 21(a) is a perspective view of a front end of the tool of FIGS. 19(a) and 19(b).
Figure 21B:
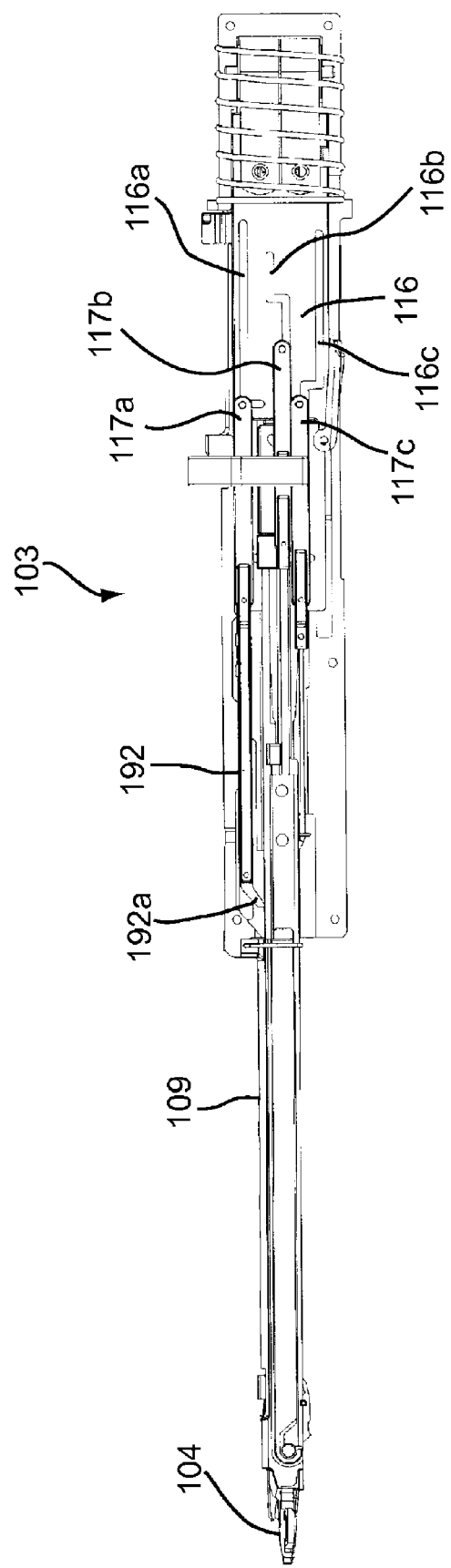
FIGS. 21(b) and 21(c) are cross-sectional side views of the front end of the tool shown in FIG. 21(a), showing left and right sides, respectively.
Figure 21C:
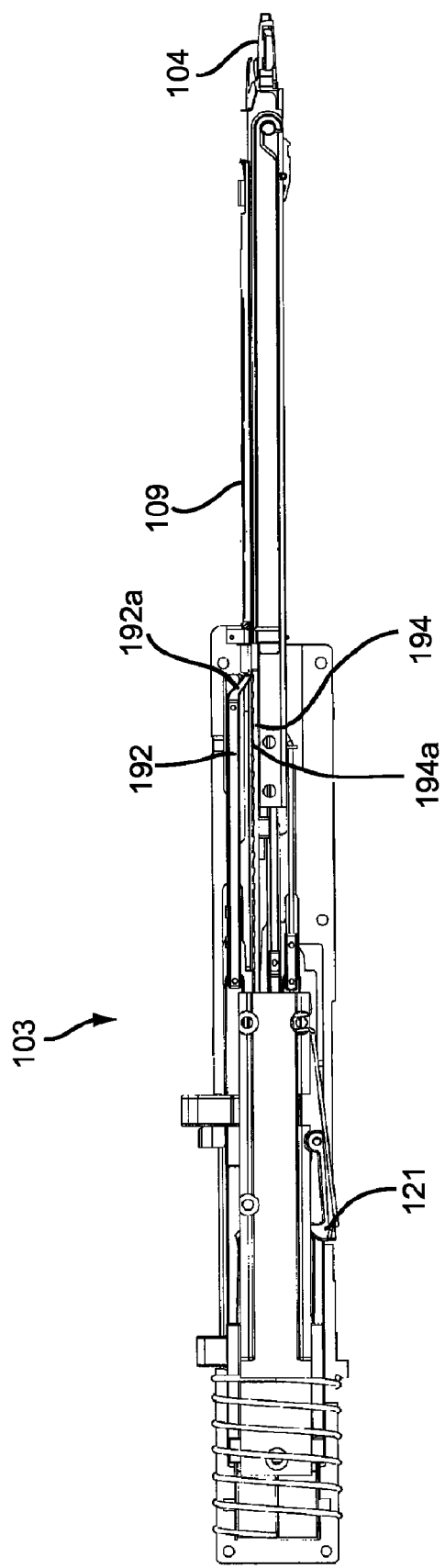

Turning to FIGS. 19(a)-21(c), another embodiment of a fastener delivery tool 102 is shown that may be used to deliver one or more fasteners (not shown), similar to previous embodiments. The tool 102 generally includes a handle 110 including a lever 112 and trigger 114, shown in FIGS. 19(a)-20(b), and an elongate shaft 109 terminating in a distal tip 104, similar to the previous embodiments. As shown in FIGS. 21(a)-21(c), the tool 102 may include one or more internal components similar to the previous embodiments, e.g., retaining member (not shown), spreader (not shown), a tongue 126, pusher member (not shown), and/or ejection track 123 within the elongate shaft 109 and/or distal tip 104. In addition, the tool 102 may include a cartridge, track, and/or other carrier (not shown), which may carry a plurality of fasteners, as described further below.

Optionally, the tool 102 may include two separate subassemblies that may be removably coupled to one another. For example, FIGS. 21(a)-21(c) show a carriage housing 103 that may be separate from the handle 110, yet may be inserted into the handle 110 to couple the actuating components of the carriage housing 103 with the lever 102 and trigger 104. The carriage housing 103 and handle 110 may include one or more cooperating connectors for securing the carriage housing 103 to the handle 110, e.g., in the proper orientation to coupled to allow the lever 112 and trigger 114 to actuate the tool 102. For example, as shown in FIG. 20(a), the carriage housing 103 may include one or more tabs 119a that may be received in corresponding slots 119b in the handle 110 to secure carriage housing 103 to the handle 110. The connectors may allow the carriage housing 103 to be removed from the handle 110, e.g., after all of the fasteners therein have been delivered, and then a new carriage housing (not shown) may then be coupled to the handle 110 to deliver additional fasteners, if desired. Alternatively, the carriage housing 103 and handle 110 may be substantially permanently attached to one another.

The components of the carriage housing 103 may be coupled to one or more of the lever 112 and/or trigger 114, similar to the embodiments described elsewhere herein. For example, the lever 112 may be generally configured similar to the lever 12 and the trigger 114 may be generally configured similar to the trigger 14, shown and described with reference to FIGS. 15(a)-15(e).

In FIGS. 19(a) and 20(a), the lever 112 may be in an unloaded position, e.g., similar to the position of lever 12 shown in FIG. 15(c). In FIGS. 19(b) and 20(b), the lever 112 has been depressed to load a fastener, e.g., from a cartridge or other carrier (not shown) within the elongate shaft 109. For example, actuation of the lever 112 may remove a fastener from a cartridge, track, or other carrier, deform the fastener from a relaxed to a constrained configuration, and advance the fastener such that tines of the fastener are exposed (not shown) from the distal tip 104, similar to the sequence shown in FIGS. 9(a)-13(b).

As best seen in FIGS. 20(a) and 20(b), the lever 112 may include a latch 113b that may be engaged by a spring or other catch 113a within the handle 104 to maintain the lever 112 in the loaded position. Thus, after the lever 112 is actuated, the lever 112 may be locked with the tips of a fastener exposed, e.g., similar to the configuration shown in FIGS. 13(a) and 13(b). This may facilitate a user manipulating the tool 102 before delivering a fastener, e.g., to test and/or otherwise identify an appropriate target location for delivering the fastener, as described elsewhere herein.

The lever 112 may be coupled to one or more ratcheted wheels 112a, 112b, which may be coupled, in turn, to the actuating components of the tool 102 via ratchet bar 112c, e.g., for loading a fastener into a loading chamber, deforming the fastener from the relaxed configuration to the U-shaped configuration, and/or for advancing the fastener down the ejection track 123. For example, as shown in FIG. 21(b), the lever 112 may be coupled via the wheel 112a and ratchet bar 112c to a drive plate 116, which may be advanced distally when the lever 112 is actuated. The drive plate 116 includes a plurality of slots 116a-116c that include arms coupled to the actuating components of the tool 102. For example, slot 116a may receive arm 117a, which may be coupled to an advancer arm 192, which may be used to advance a belt assembly or other track (not shown), as explained further below.

Slot 116b may slidably receive 117b, which may be coupled to the pusher member (not shown), and slot 116c may receive arm 117c, which may be coupled to the spreader (not shown). Another slot (not shown) may be provided on the drive plate 116 that may receive an arm (also not shown) coupled to the tongue (not shown). When the lever 112 is actuated, the drive plate 116 may be directed distally within the carriage assembly 103, thereby directing the arms distally until cams drop the arms out of vertical portions of the slots 116a-116c and into horizontal portions thereof. The sequence of the slots 116a-116c and arms 117 may function similarly to the sequence described in the previous embodiments.

Once the lever 112 is actuated and the user decides to deliver the fastener, the trigger 114 may be actuated similar to the trigger 14, as described elsewhere herein. For example, when the lever 112 is actuated, a spring (not shown) may be compressed, similar to spring 36 shown in FIGS. 13(a)-14(b), to store potential energy. When the lever 112 is fully actuated, a lock 121 may engage to prevent the energy from the spring being released. When the trigger 114 is actuated, the lock 121 may be released, and the spring may rapidly advance the pusher member (not shown) to eject the fastener from the tool 102, similar to the action of the pusher member 30 described above. In addition, actuation of the trigger 114 may "reset" the tool 102, e.g., in preparation for loading and delivering another fastener. For example, when the trigger 114 is actuated, a latch 113c may engage a cam 114 to release the spring 113 from the latch 113b, thereby allowing the lever 112 to return to its original position.

Optionally, the front end of the tool 102 may include a cover or other housing (not shown), e.g., over the elongate shaft 109 and/or distal tip 104. The cover may provide a desired aesthetic finish to the tool 102 and/or may protect the interior components. In addition, the cover may provide access to the interior of the elongate shaft 109, e.g., to remove and/or load a cartridge or other carrier (not shown in FIGS. 21(a)-21(c)) into the tool 102, as described further below. Thus, the tool 102 may allow multiple fasteners to be delivered successively using the tool 102 without having to reload individual fasteners. For example, the cover or housing on the elongate shaft 109 may be opened or otherwise removed to allow a belt assembly or other cartridge (not shown, carrying a plurality of fasteners) to be loaded into the tool 102. Alternatively, the cover may be opened to allow individual fasteners to be loaded onto a belt or other track (not shown) in the elongate shaft 109. In a further alternative, the cover may not be removable; in this alternative, the tool 102 may included a belt assembly or track pre-loaded with a plurality of fasteners that may delivered with the tool 102. Once the supply of fasteners is depleted, the tool 102 may be discarded or returned to the manufacturer for reloading.

Turning to FIGS. 22-27(c), another embodiment of a tool 202 is shown that includes a handle 210, an elongate shaft 209, and a distal tip 204 (including actuating components therein), which may include similar components to the other embodiments described herein. Unlike the previous embodiments, the tool 202 includes an air cylinder 213 for actuating the tool 202, e.g., to load and/or fire one or more fasteners successively using the tool 202. FIGS. 23(a)-23(c) show additional details of the tool 202, e.g., including a trigger, firing button or other actuator 212 on the handle 210 that may be used to activate the air cylinder 213 to deliver a fastener from the tool 202. The firing button 212 may completely deliver a fastener upon activation of the trigger 212. Alternatively, the firing button 212 (or separate actuators, not shown) may allow a two-stage delivery, e.g., loading and partially exposing a fastener upon initial actuation, and then releasing the fastener upon final actuation, similar to the previous embodiments.

For example, a compressed air, carbon dioxide, or other fluid line (not shown) may be coupled to a connector 213a on the air cylinder 213 to at least partially actuate the tool 202. The fluid line may include a pedal, valve, or other actuator, which may be opened to deliver fluid into the air cylinder 213. This action causes the tool 212 to load a fastener from the cartridge or track, deform the tool, and advance the fastener down the ejector track 223, similar to the lever 112. When the user is ready to deliver the fastener, the firing button 212 may be depressed to eject the fastener. The user may then open the fluid line again to load the next fastener for delivery. It will be appreciated that any pneumatic or hydraulic system may be used to load the fasteners. Alternatively, the fluid line may automatically load a fastener without requiring the user to activate the fluid line. In a further alternative, a self-contained compressed fluid device may be provided in the handle 210 of the tool 202, which may be activated or may automatically load a fastener.

Figure 24A:
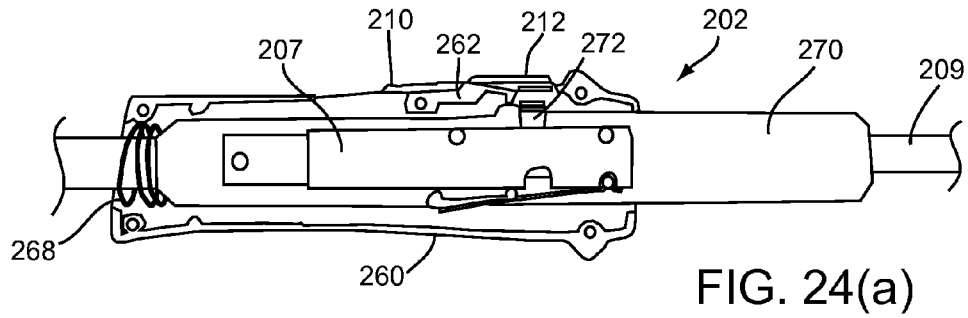
FIGS. 24(a) and 24(b) are top views of the tool of FIG. 22 with a cover removed to show a cartridge assembly carrying fasteners therein.
Figure 24B:
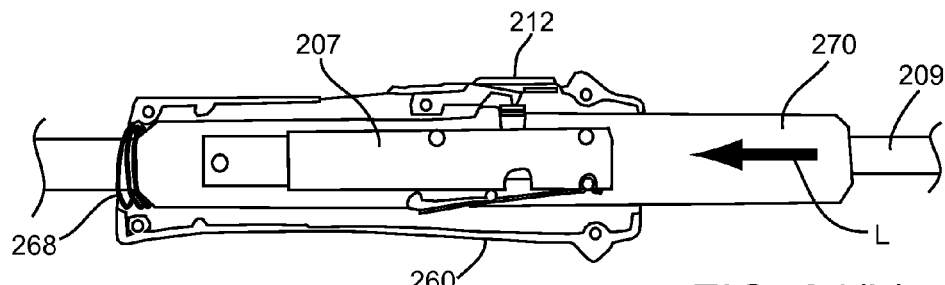

Turning to FIGS. 24(a)-25(b), similar to the previous tool 102, the tool 202 may include a reusable portion, i.e., the handle 210, and a disposable portion, i.e., a carriage housing 207 that may be loaded into the handle 210 for providing a plurality of fasteners (not shown) to be delivered by the tool 202. For example, as shown in FIGS. 24(a) and 24(b), the handle 210 includes a cover 260 over a housing 270 that includes the internal actuating components of the handle 210, e.g., coupling the firing button 212 to the air cylinder 213. The housing 270 may be movable axially within the cover 260, e.g., between a first or "locked out" position, shown in FIG. 24(a) and a second or "active" position, shown in FIG. 24(b). As shown in FIGS. 24(a) and 24(b), a spring 268 may be provided between the housing 266 and the cover 260 for biasing the housing 270 to the locked out position, yet the bias may be overcome when the carriage housing 207 is loaded into the handle 210.

The carriage housing 207 includes a proximal housing 208, e.g., including a drive plate (not shown) or other actuating components, the elongate shaft 209, and distal tip 204 of the tool 202, which may include an ejection track 223, retaining member, spreader, tongue, and/or pusher member (all not shown), which may operate generally similar to the previous embodiments. The cover 260 may include an open end opposite the air cylinder 213 into which the carriage housing 207 may be inserted to couple the actuating components of the carriage housing 207 to the handle 210. Alternatively, the elongate shaft 209 and distal tip 204 may be part of the handle 210 and a belt assembly or other cartridge assembly (not shown) may be loaded directly into the elongate shaft 209 and/or proximal housing 208.

Figures 25A, 25B:
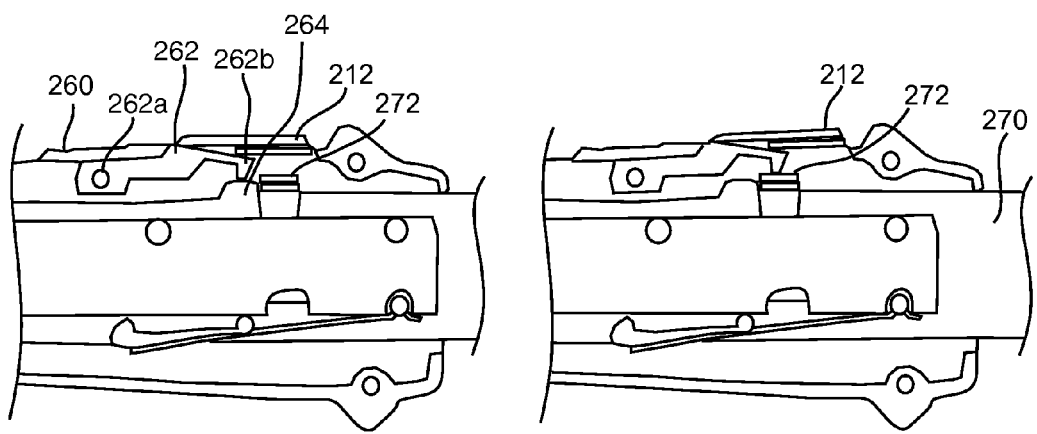
FIGS. 25(a) and 25(b) are details of the tool of FIGS. 24(a) and 24(b) showing a firing button being locked out to prevent latch actuation and engaged to permit latch actuation, respectively.

The handle 210 may include features to ensure that the carriage housing 207 is properly loaded into and/or otherwise coupled to the handle 210. For example, FIGS. 25(a) and 25(b) show a lever arm 262 that includes a pivotable end 262a and a free end 262b underlying the firing button 212. Before the carriage housing 207 is properly received in the handle 210, the free end 262b of the lever arm 262 abuts a hub 264 on the housing 270, as shown in FIG. 25(a). Thus, in this position, the firing button 212 cannot be depressed because the lever arm 262 cannot be directed inwardly. As the carriage housing 207 is loaded into the housing 270, i.e., inserted in the direction of arrow "L" shown in FIG. 24(b), the housing 270 is displaced axially against the bias of the spring 268, thereby directing the hub 264 proximally from under the free end 262b of the lever arm 262. Once the carriage housing 207 is properly seated in the handle 210, the free end 262b of the lever arm 262 may overly the latch 272, as shown in FIG. 25(b). When the firing button 212 is then depressed, the lever arm 262 may pivot inwardly until the free end 262b contacts and pushes the latch 272, allowing fasteners to be delivered from the tool 202. Thus, without the latch 272 properly engaged, the firing button 212 may be locked out, e.g., preventing fasteners from moving within and/or being delivered from the tool 202 and/or otherwise risking damage to the tool 202 and/or injury to the user due to accidental activation of the air cylinder 213.

The carriage housing 207 and handle 210 may include cooperating connectors (not shown) that may secure the carriage housing 207 to the housing 270 and/or that secure the housing 270 in the active position relative to the cover 210. For example, the carriage housing 207 and handle 210 may include tab 219a and slot 219b, similar to the previous embodiments. When the carriage housing 207 is connected to the handle 210, the internal actuating components of the handle 210 may be coupled to the actuating components within the elongate shaft 209 of the carriage housing 207. When the fasteners within the carriage housing 207 are depleted or it is other desired to remove the carriage housing 207, the connectors may be released, returning the handle 210 to the locked out position.

Figure 22:
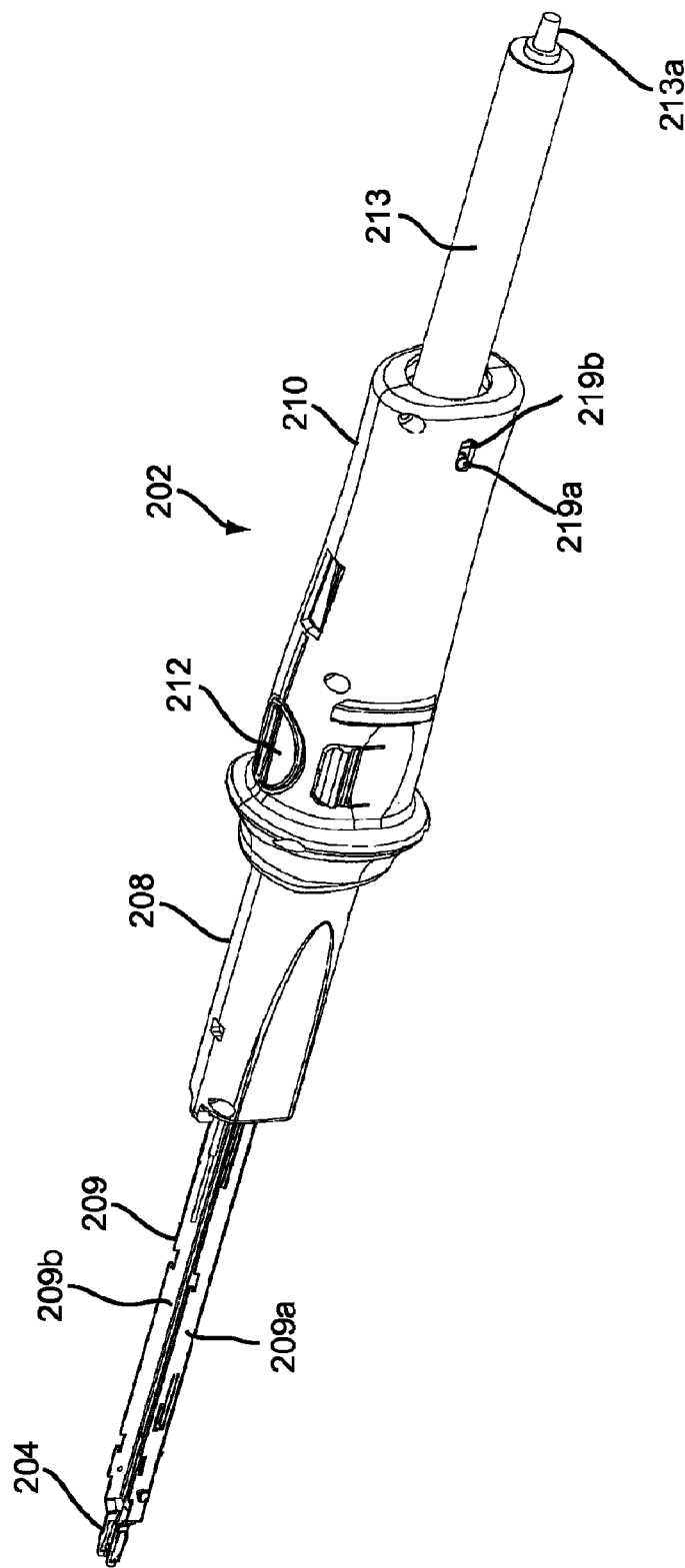
FIG. 22 is a perspective view of an alternate embodiment of a fastener delivery tool including a pneumatic actuator.
Figure 23A:
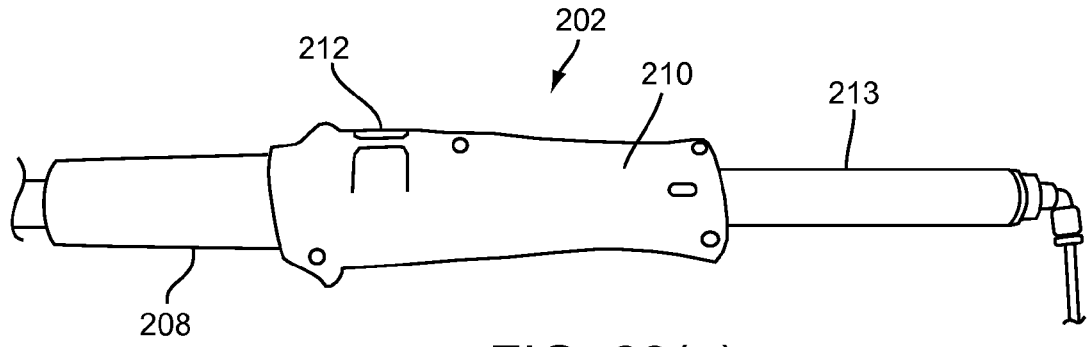
FIGS. 23(a)-23(c) are side and top views of the tool of FIG. 22.
Figure 23B:
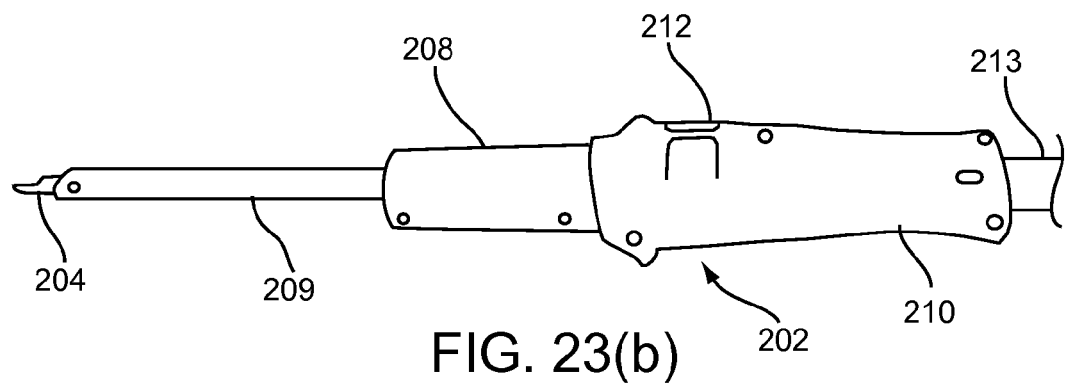
Figure 23C:
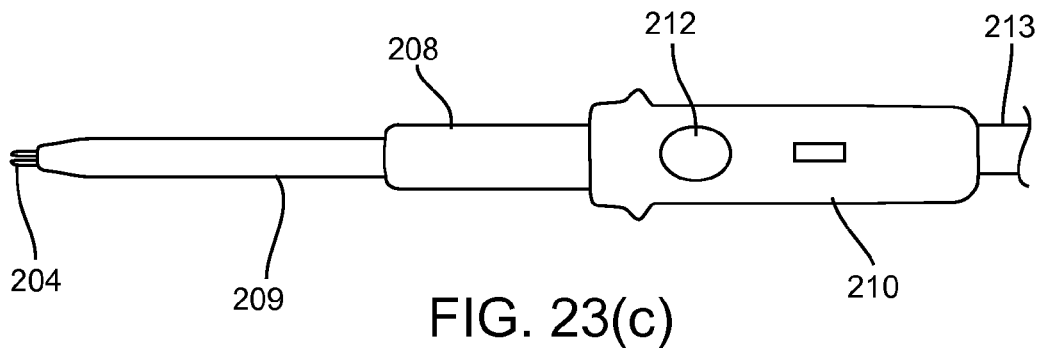
Figure 26A:
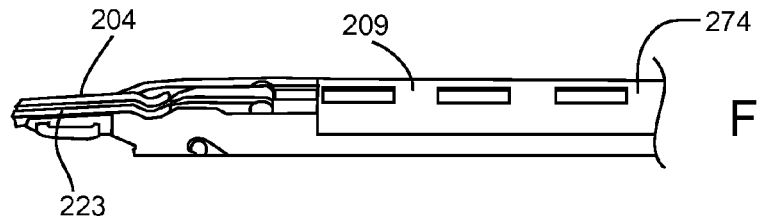
FIGS. 26(a) and 26(b) are details of a front end of the tool of FIG. 22 with a cover mounted over and removed from the front end, respectively, showing fasteners being carried within the front end.
Figure 26B:
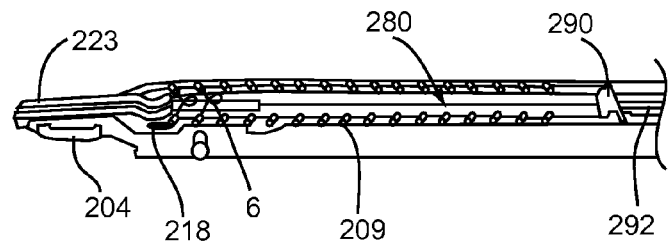
Figure 27A:
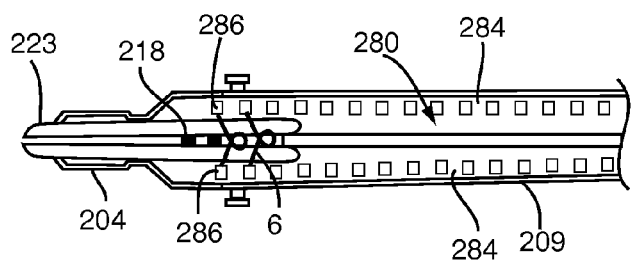
FIGS. 27(a)-27(c) are additional details of the front end of the tool of FIG. 22.
Figure 27B:
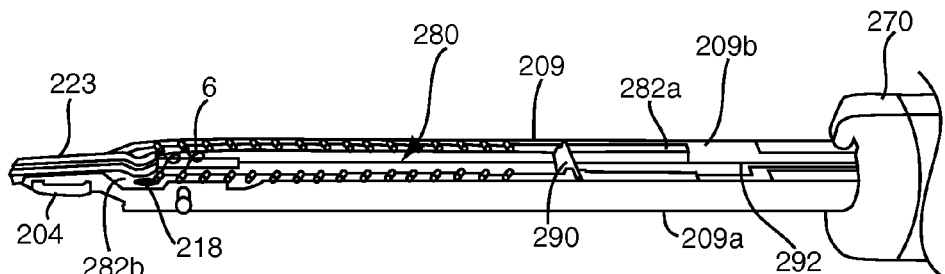
Figure 27C:
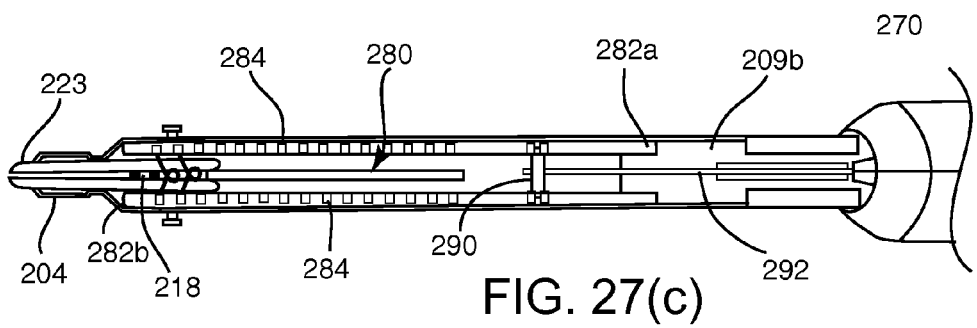
Figure 28A:
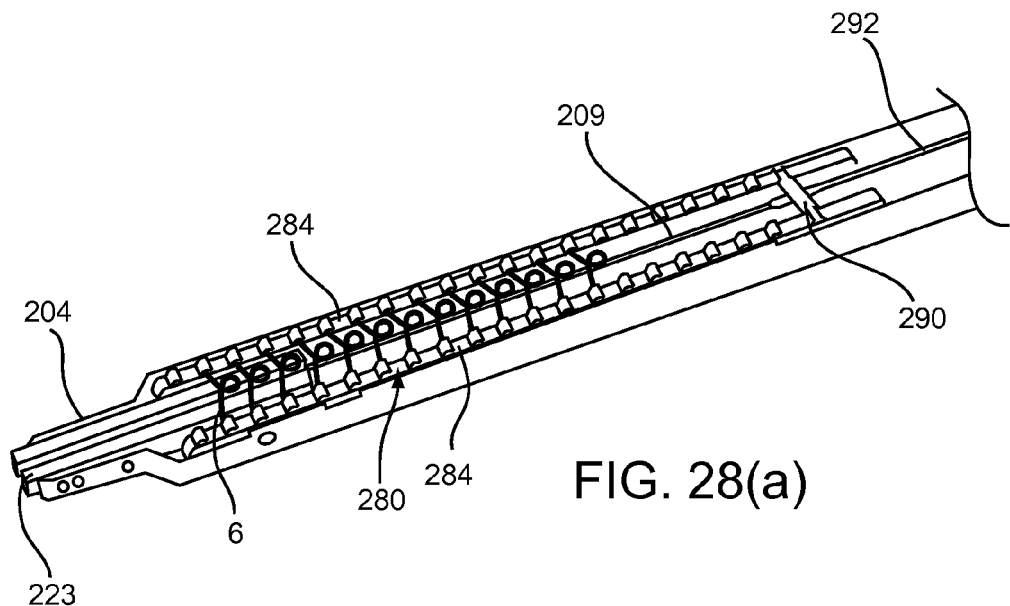
FIGS. 28(a) and 28(b) are perspective views of a distal end that may be provided on the fastener delivery tools of FIGS. 19(a)-21(c) or FIGS. 22-27(c).
Figure 28C:
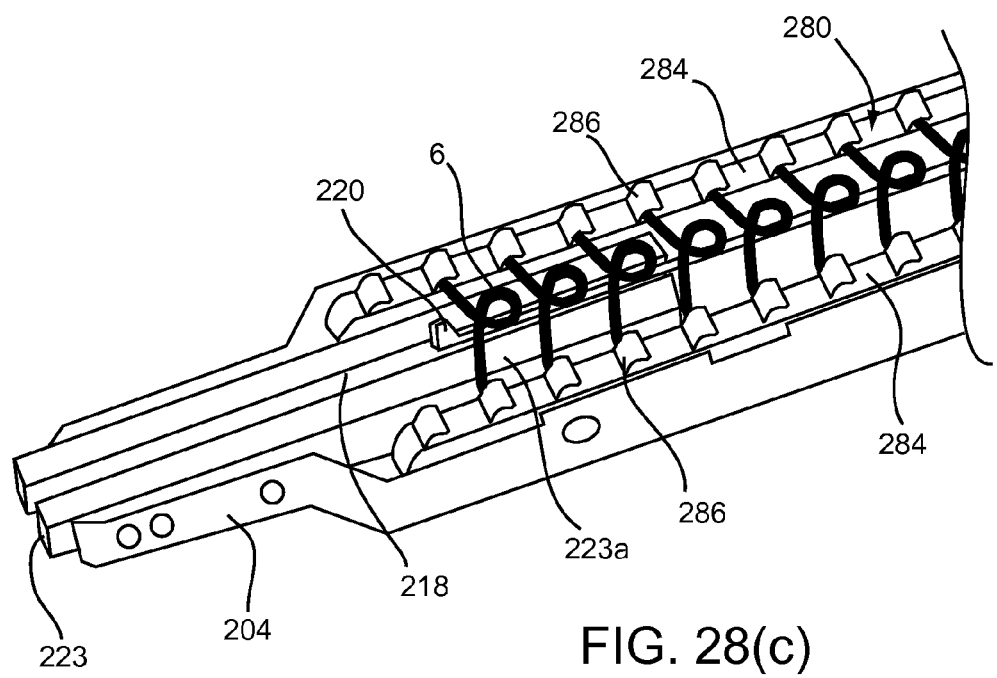
FIG. 28(c) is a detail of the distal end of FIG. 28(a), showing a plurality of fasteners carried by a belt.
Figure 28B:
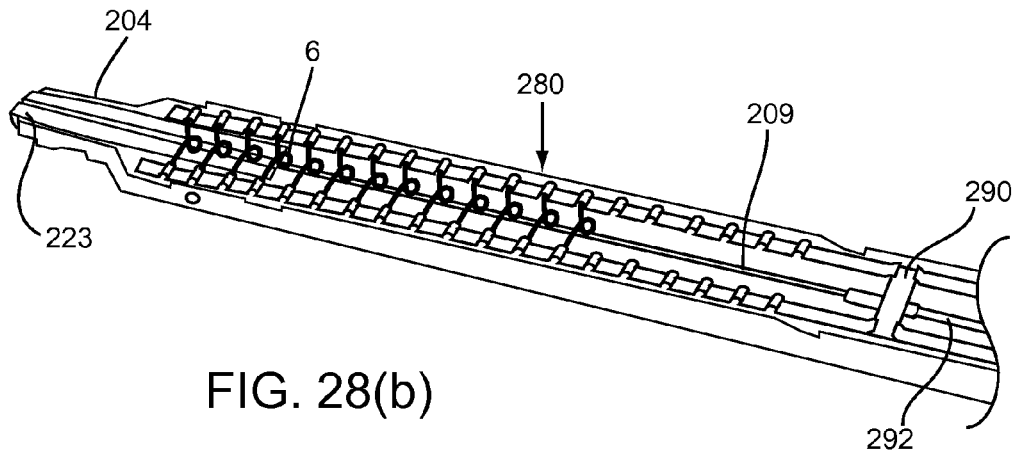

Turning to FIGS. 26(a)-28(c), the elongate shaft 209 of the tool 202 is shown in more detail. Generally, the elongate shaft 209 includes a belt assembly 280 for carrying a plurality of fasteners 6 to the loading chamber 218 in the distal tip 204 of the tool 202. FIG. 26(a) shows the elongate shaft 209 with a cover 274 attached over the belt assembly 280 (and other internal components), while FIG. 26(b) shows the cover 274 removed to expose the belt assembly 280. As best seen in FIGS. 22, 27(b), and 27(c), the elongate shaft 209 includes a rigid elongate base or chassis 209a defining a channel 209b that extends from a first end of the carriage housing 207 (received in the housing 270) to the distal tip 204. An ejection track 223, e.g., including a pair of spaced-apart rails having a "C" shaped cross-section, extends from the loading chamber 218 for guiding the fasteners 6 during delivery. As best seen in FIG. 28(c), a retaining pin 220 is provided in the loading chamber 218 for receiving each fastener 6 successively from the belt assembly 280, as described further below. A spreader, tongue, and pusher member (not shown) are also provided within the elongate shaft 209 and/or distal end 204 that operate generally similar to the previous embodiments.

Figure 29A:
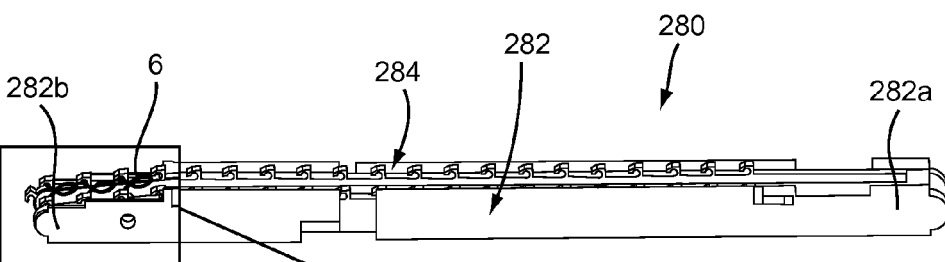
FIGS. 29(a) and 29(b) are side and perspective views, respectively, of a belt assembly that may be mounted in the distal end shown in FIGS. 28(a)-28(c).
Figure 29C:
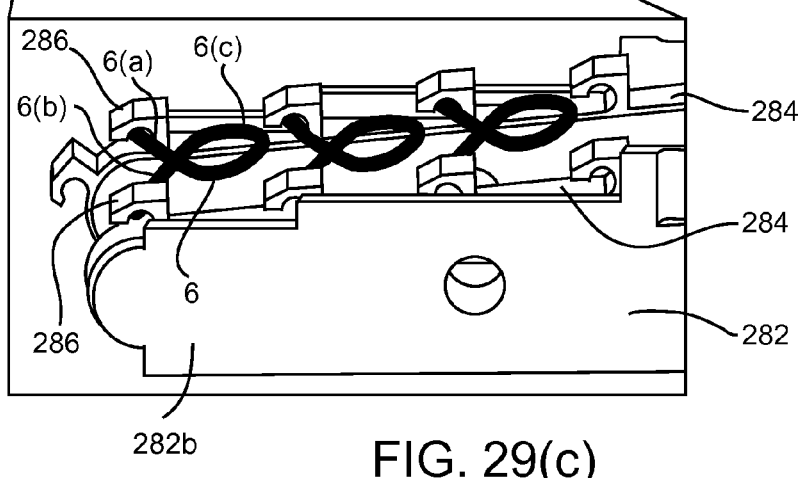
FIG. 29(c) is a detail of the belt assembly of FIG. 29(a).
Figure 29B:
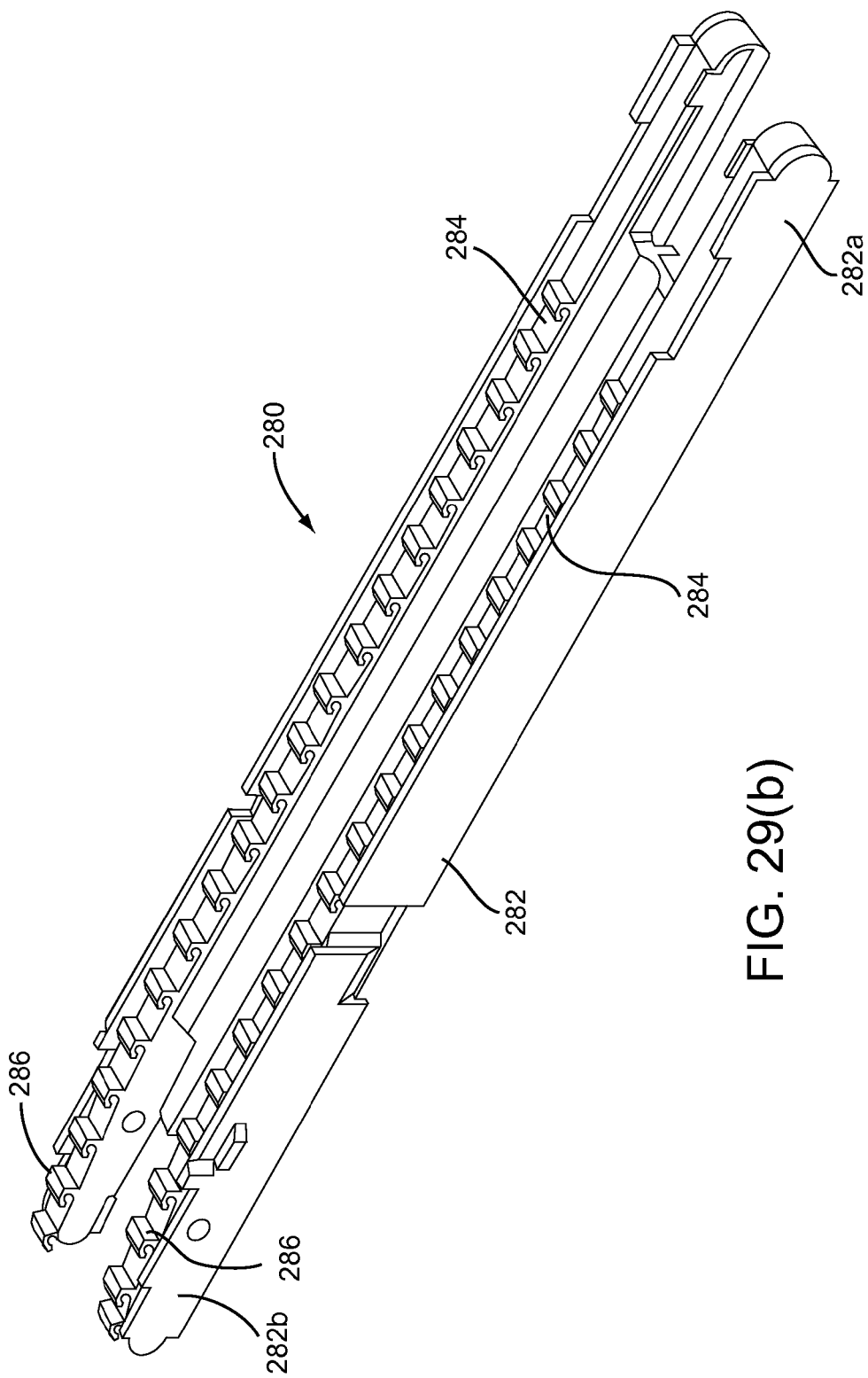

With additional reference to FIGS. 29(a)-29(c), the belt assembly 280 generally includes a frame 282 and a pair of belts 284 movable relative to the frame 282. The frame 282 includes a first end 282a, which may be disposed within the chassis 209a (e.g., nearest the housing 270, as shown in FIGS. 27(b) and 27(c)), and a second end 282b, which may be disposed adjacent the distal tip 204 and/or loading chamber 218. The frame 282 may be substantially secured within the channel 209b of the chassis 209a, e.g., using one or more cooperating connectors (not shown), bonding with adhesive, interference fit, and the like, such that the frame 282 remains substantially stationary during use.

Each belt 284 may be an endless band or loop received around hubs (not shown) on the first and second ends 282a, 282b of the frame 282. Thus, the belts 284 may be free to move, e.g., such that upper surfaces of the belts 284 may be directed distally towards the loading chamber 218, while simultaneously lower surfaces of the belts 284 are directed proximally away from the loading chamber 218. The hubs may include wheels or other features on axles (not shown) to facilitate movement of the belts 284. Alternatively, each belt 284 and/or the hubs of the frame 284 may be formed from material minimizing friction between the belts 284 and the hubs, e.g., including a lubricious coating or material, such that the belts 284 may slide easily around the hubs. In an exemplary embodiment, each belt 284 may made from a strip of substantially inelastic material, e.g., a metal, polymer, and/or composite material, having sufficient flexibility to be curved around the ends 282a, 282b of the frame 282 and having sufficient length such that ends of the strip may be attached to one another, e.g., by bonding with adhesive, sonic welding, mating connectors (not shown), and the like, to create the band or loop. Alternatively, a single belt (not shown) may be provided that extends across the width of the frame 282, rather than separate belts 284. In a further alternative, the belt may be made from one or two strips (not shown) having a first end fixed to a track supported by the frame 282 below the loading chamber 218 and a second end fixed to the track adjacent the first end 282a of the frame 282.

Each of the belts 284 include features for receiving a portion of fasteners 6 loaded onto the belt assembly 280, e.g., to releasably carry the fasteners 6 along the belt assembly 280 to the loading chamber 218 of the tool 202. For example, as best seen in FIG. 29(c), each belt 284 includes a plurality of hooks 286 for receiving tines 6(a), 6(b) of respective fasteners 6. The hooks 286 may be formed directly in the belt material, e.g., by injection molding, machining, and the like, or may be separate from the belts 284 and attached thereto, e.g., by bonding with adhesive, sonic welding, cooperating connectors (not shown), and the like. The hooks 286 may define a recess sized for receiving the tines 6(a), 6(b) therein, e.g., the hooks 286 extending at least about one hundred eight degrees (180°) around the recess. The hooks 286 may be sufficiently flexible to allow the tines 6(a), 6(b) to be released from the recesses when a loop portion 6(c) is received around the retaining pin 220, e.g., when the first fastener 6 on the belt assembly 280 is advanced into the loading chamber 218. In addition, the ejector track 223 may include ramped proximal edges to guide the fastener 6 from the belts 284 onto the retaining pin 220.

The belts 284 may be advanced by an actuator coupled to the handle 210. For example, as shown in FIGS. 27(b), 27(c), 28(b), and 28(c), a cross-bar 290 may be attached between the belts 284, e.g., thereby coupling movement of the belts 284 together. In addition, the cross-bar 290 may maintain the hooks 286 in adjacent pairs to ensure that individual fasteners 6 may be releasably captured by respective pairs of hooks 286. A pushrod 292 may be coupled to the cross-bar 290, e.g., to advance the belts 284 with each actuation of the tool 202. For example, the pushrod 292 may be advanced initially to direct the first fastener 6 into the loading chamber 218, e.g., such that the loop portion 6(c) is received on the retaining pin 220 (see FIG. 28(c). When the firing button 212 (or the lever 112 of the tool 102) is actuated, the fastener 6 may be deformed into the U-shaped configuration and advanced down the ejector track 223 (or 123), similar to the previous embodiments. When the fastener 6 is ejected from the ejector track 223 (or 123), the pushrod 292 may be advanced sufficiently to deliver the next fastener 6 into the loading chamber 218 and/or onto the retaining pin 220.

Alternatively, the pushrod may be retracted and advanced between fasteners. For example, as shown in FIGS. 21(b) and 21(c), an advancer arm 192 may be provided within the tool 102, e.g., within the carriage housing 103 of FIGS. 21(b) and 21(c) or within the proximal housing 208 of FIG. 22. The advancer arm that may include a tip 192a that may contact elements on a track 194 to which the pushrod 292 is coupled to advance the fasteners. For example, the tip 192a may contact blunt edges of recesses 194a in the track 194 during advancement, and may slide proximally over the recesses 194a during retraction. Thus, when the lever 102 is initially depressed, the advancer arm 192 may be advanced a predetermined distance corresponding to the spacing of the fasteners on the belts, and the tip 192a may engage the immediately adjacent recess 194a to advance the track 194. The track 194 in turn advances the pushrod 292, which advances the belts 284, e.g., shown in FIGS. 27(a)-27(c). The lever 112 may then deform and advance the fastener down the ejector track 123. The advancer arm 192 may be retracted immediately after pushing the lever 112 or after actuating the trigger 114, thereby pulling the tip 192a back adjacent the next recess 194a in the track 194 Thus, the track 194 may be advanced incrementally, advancing the pushrod and belts 284.

Accordingly, a belt assembly may be provided in a disposable (or reusable) assembly that may be coupled to a handle or other actuator, such as the carriage housing 207 described above for the tool 202. Alternatively, a belt assembly may be provided within a tool that cannot be reloaded. For example, if the carriage housing 103 is not removable from the tool 102, after the fasteners are all delivered, the entire tool 102 may be discarded or reused (e.g., by returning the tool 102 to the manufacturer who may sterilize and reload the tool 102 with new fasteners). In a further alternative, the chassis or elongate shaft may include a cover that may be removed or otherwise opened to allow a belt assembly to be replaced or to allow individual fasteners to be loaded on a belt assembly. In this alternative, the frame of the belt assembly and/or the elongate shaft may include one or more connectors for removably securing the belt assembly within the elongate shaft. Otherwise, operation of this alternative may proceed similar to the other embodiments described herein.

Figure 30:
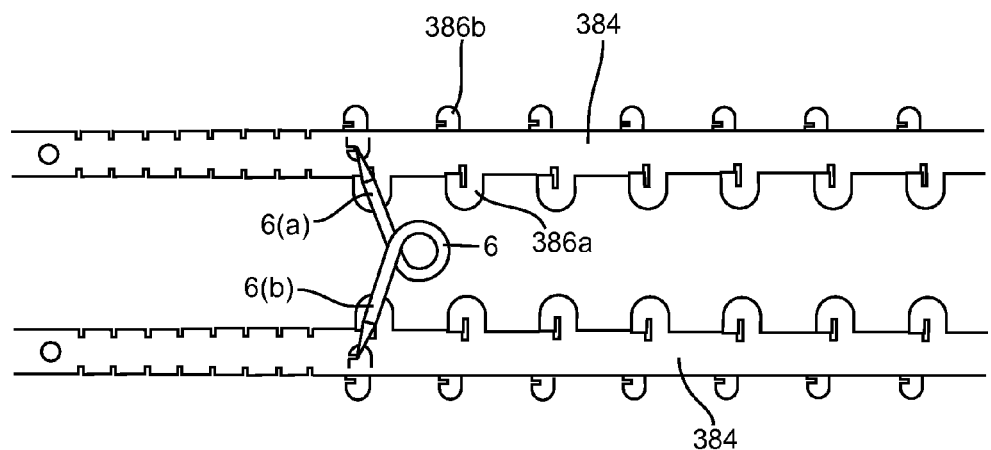
FIG. 30 is a top view of an exemplary embodiment of a pair of belts that may be included in the belt assembly of FIGS. 29(a)-29(c).

Turning to FIG. 30, another embodiment of a pair of belts 384 are shown that may be provided in a belt assembly (not shown) in any of the embodiments described herein. As shown, each belt 384 is an elongate strip that may be wrapped around hubs on a frame, similar to the belts 284 described above. Each belt 384 includes features 386a, 386b that may be folded up to receive tines 6(a), 6(b) of fasteners 6 thereunder. For example, each belt 384 may include partial loops or "J" hooks 386a that may be lifted to be received over and/or around the tines 6(a), 6(b). The "J" hooks 386a may be disposed along edges of the belts 384 nearest each other to receive a middle portion of the tines 6(a), 6(b) thereunder. Each belt 384 may also include tabs 386b with slots or holes to receive the tips of the tines 6(a), 6(b), e.g., along edges of the belts 384 away from each other. Each belt 384 may be formed from a thin film, e.g., by laser cutting, stamping, mechanically cutting, and the like, such that the features 386a, 386b are formed directly in the film with the respective belts 384. Any other features needed for each belt 384 may also be formed directly in the film, e.g., holes or slots for connecting ends of the belt 384 together after wrapping the belt 384 around the frame of the belt assembly.

Figure 31B:
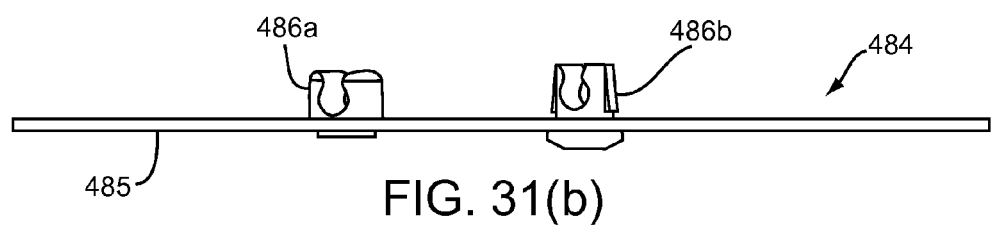
FIGS. 31(a) and 31(b) are top and side views, respectively, of another exemplary embodiment of a belt that may be included in a belt assembly, showing alternative embodiments of clip features for receiving legs of a fastener carried by the belt assembly.
Figure 31C:
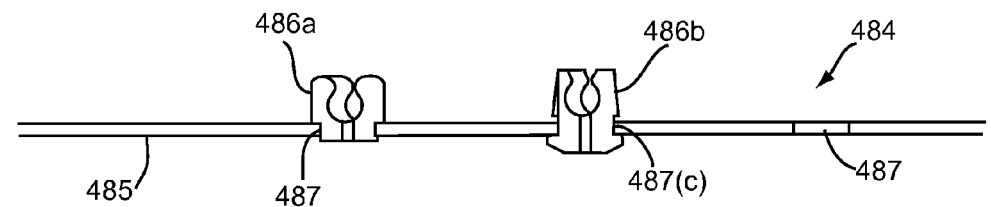
FIG. 31(c) is a cross-section through the belt of FIG. 31(a), taken along line 31(c)-31(c).
Figure 31A:
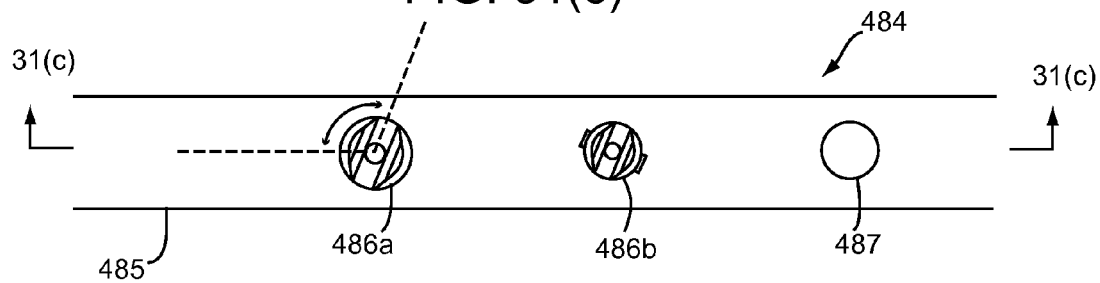

Turning to FIGS. 31(a)-31(c), another embodiment of a belt 484 is shown that may provided in a belt assembly for any of the embodiments described elsewhere herein. As shown, the belt 484 includes a band 485, e.g., made from a metal, plastic, or composite material sufficiently flexible to be movably mounted around a frame of a belt assembly, similar to the previous embodiments. For example, the band 485 may be laser cut, stamped, mechanically cut, molded, and the like to include spaced-apart openings 487 therein for receiving features 486a, 486b. The features 486a, 486b may be clips, e.g., formed from plastic, metal, or composite materials, that may be attached to the band 485, e.g., in respective holes 487. For example, the clip 486a may be inserted into hole 487 and secured therein, e.g., by heat-stake, bonding with adhesive, sonic welding, press-fit, and the like. The clip 486b (which may be used instead of the clip 486a in a belt 484) may be snapped into the hole 487 or secured similar to clip 486a.

Figure 32:
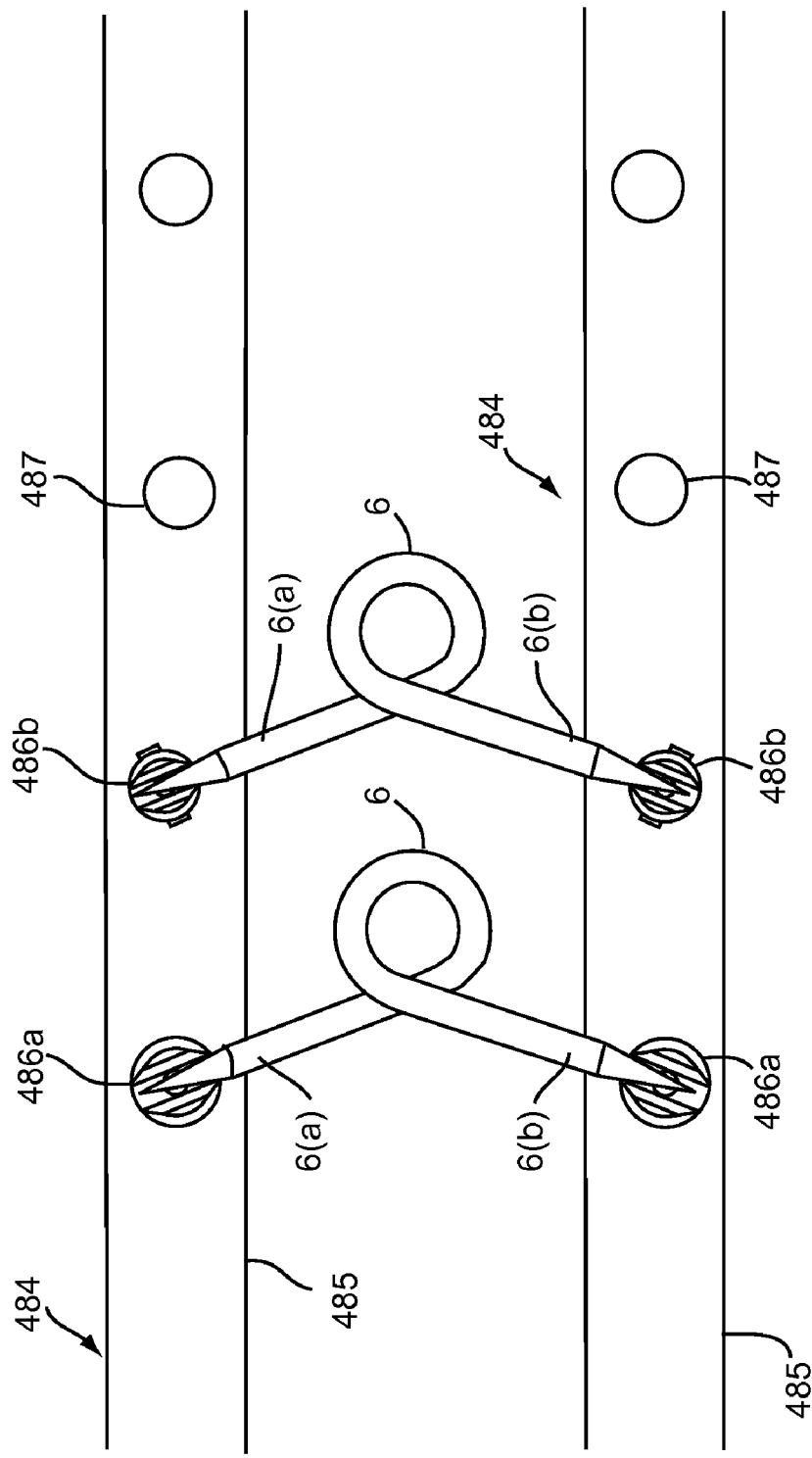
FIG. 32 is a top view of a pair of belts, similar to the embodiment of FIGS. 31(a)-31(c) carrying a plurality of fasteners.

As shown in FIG. 32, a pair of belts 484 may be provided, e.g., in a belt assembly (not shown) for carrying a plurality of fasteners 6, similar to the previous embodiments. The clips 486a, 486b may be aligned in pairs for receiving respective tines 6(a), 6(b) of fasteners 6, e.g., within recesses or slots in the clips 486a, 486b. Unlike the recesses in the hooks 286, which extend laterally, the slots in the clips 486a, 486b may extend substantially vertically, i.e., upwardly away from the bands 485. Otherwise, the clips 486a, 486b and hooks 286 may be used similarly to one another.

It will be appreciated that any of the features described herein should substantially securely hold the fasteners carried by the belt assembly, e.g., to prevent the fasteners from coming loose during normal operation of the delivery tool. However, the features should allow the fasteners to be released easily from the belt assembly as they are delivered into the loading chamber, e.g., without risk of jamming the tool. In addition, it may be desirable that the materials of the belt assembly contacting the fasteners be non-metallic, e.g., to reduce the risk of damaging the fasteners while being carried by the belt assembly. For example, it may be desirable to make the components contacting the fasteners, such as the belts themselves and/or the features capturing the tines, from PEEK, e.g., PEEK Classix. This may reduce the risk of the belt scratching or otherwise creating any surface defects in the fasteners.

While embodiments of the present invention have been shown and described, various modifications may be made without departing from the scope of the present invention. The invention, therefore, should not be limited, except to the following claims, and their equivalents.

We claim:

1. A fastener delivery tool, comprising:
 a belt comprising a pair of features configured to releasably engage tines of a fastener in a relaxed state;
 a retaining member configured to receive the fastener and to retain the fastener in a first position with respect to the fastener delivery tool;
 a tongue configured to transform the fastener into a constrained state by spreading the tines apart by advancing distally along inner surfaces of the tines while the fastener is retained in the first position;
 a pusher member configured to advance distally in unison with the tongue to push the fastener from the first position to a second position; wherein the retaining member is configured to release the fastener in response to interaction of a cam with the pusher member.

2. The fastener delivery tool of claim 1, wherein the pusher member is configured to advance distally with respect to the tongue to eject the fastener from a distal tip of an ejection track.

3. The fastener delivery tool of claim 1, further comprising a fastener comprising tines,
 wherein, in the relaxed state, the tines of the fastener overlap one another to define a loop, and, in the constrained state, the fastener defines a U-shape.

4. The fastener delivery tool of claim 1, further comprising an ejection track comprising side walls configured to constrain the fastener in the constrained state as the fastener is advanced down the ejection track to the second position.

5. The fastener delivery tool of claim 4, wherein, in the second position, the tines are exposed distally beyond the ejection track without being ejected completely from the ejection track.

6. The fastener delivery tool of claim 1, wherein the retaining member is configured to retain the fastener by protruding through a loop of the fastener.

7. The fastener delivery tool of claim 6, wherein the retaining member is coupled to at least one of the tongue and the pusher member such that the retaining member is configured to release the fastener in response to advancement of the pusher member.

8. The fastener delivery tool of claim 1, further comprising a staging section including a plurality of fasteners disposed therein.

9. The fastener delivery tool of claim 8, wherein the plurality of fasteners are carried by a cartridge receivable in the staging section.

10. The fastener delivery tool of claim 1, wherein the cam is located on the retaining member.

11. The fastener delivery tool of claim 1, further comprising a spreader configured to transform the fastener into a partially constrained state by spreading the tines.

12. The fastener delivery tool of claim 1, wherein the tongue is configured to transform the fastener into the constrained state by advancing distally along inner surfaces of the tines from a proximal end of the fastener to a distal end of the fastener.

13. The fastener delivery tool of claim 1, wherein the pusher member and the tongue are configured to advance in response to movement of an actuator.

14. A fastener delivery tool, comprising:
a housing comprising an actuator;
a cartridge assembly extending from the housing and carrying a plurality of fasteners, the cartridge assembly comprising a belt comprising pairs of features releasably engaging tines of respective fasteners in a relaxed state, each of the fasteners defining a loop in the relaxed state;
a loading chamber for successively receiving a fastener from the belt in the relaxed state;
a retaining member configured to retain the fastener within the loading chamber;
an ejection track communicating with the loading chamber;
a tongue coupled to the actuator and configured to transform the fastener into a U-shaped constrained state by spreading the tines apart by advancing distally along inner surfaces of the tines in response to activation of the actuator; and
a pusher member coupled to the actuator and configured to advance distally in unison with the tongue to advance the fastener from the loading chamber down the ejection track in response to activation of the actuator,
wherein the belt is configured to deliver another fastener within the loading chamber in response to activation of the actuator.

15. The fastener delivery tool of claim 14, wherein the cartridge assembly is removable from the housing such that a new cartridge assembly carrying a plurality of fasteners is connectable to the housing.

16. The fastener delivery tool of claim 14, wherein the cartridge assembly is connectable to the housing, and wherein the belt, retaining member, tongue, and pusher member are configured to be coupled to the actuator after the cartridge assembly is connected to the housing.

17. The fastener delivery tool of claim 14, wherein the actuator comprises a first actuator configured to advance the tongue and the pusher member, and a second actuator configured to eject the fastener from the ejection track.

18. The fastener delivery tool of claim 14, wherein the actuator comprises an air cylinder.

19. The fastener delivery tool of claim 14, wherein the cartridge assembly is connectable to the housing, and wherein the housing comprises a lockout feature that prevents actuation of the actuator when the cartridge assembly is not connected to the housing.

20. The fastener delivery tool of claim 19, wherein the lockout feature comprises a lever arm that is locked to prevent the actuator from being actuated before the cartridge assembly is connected to the housing, the lever arm being coupled to a latch when the cartridge assembly is connected to the housing such that activation of the actuator activates the latch to deliver a fastener from the ejection track.

21. The fastener delivery tool of claim 14, wherein the cartridge assembly comprises a frame comprising first and second ends, the second end disposed adjacent the loading chamber, and wherein the belt comprises a pair of endless bands extending between the first and second ends of the frame, each band comprising a plurality of features disposed adjacent features of the other band.

22. The fastener delivery tool of claim 21, further comprising a cross-bar coupling movement of the pair of endless bands together, and a pushrod coupled to the actuator and configured to advance the cross-bar to simultaneously advance the pair of endless bands.

23. The fastener delivery tool of claim 14, wherein the features comprise one of hooks and clips defining recesses configured to releasably receive the tines therein.

24. A fastener delivery tool, comprising:
a housing comprising an actuator;
an elongate shaft extending from the housing and terminating in a distal tip, the shaft comprising a belt assembly therein comprising pairs of features releasably engaging tines of respective fasteners in a relaxed state, each of the fasteners defining a loop in the relaxed state;
a loading chamber in the distal tip for successively receiving a fastener from the belt in the relaxed state;
a retaining member configured to retain the fastener within the loading chamber;
an ejection track communicating with the loading chamber;
a tongue coupled to the actuator and configured to transform the fastener into a U-shaped constrained state by spreading the tines apart by advancing distally along inner surfaces of the tines in response to activation of the actuator; and
a pusher member coupled to the actuator and configured to advance distally in unison with the tongue to advance the fastener from the loading chamber down the ejection track in response to activation of the actuator,
wherein the belt is configured to deliver another fastener within the loading chamber in response to activation of the actuator.

25. The fastener delivery tool of claim 24, wherein the belt assembly comprises a pair of endless bands, each band comprising a plurality of features disposed adjacent features of the other band.

26. The fastener delivery tool of claim 25, further comprising a cross-bar coupling movement of the pair of endless bands together, and a pushrod coupled to the actuator and configured to advance the cross-bar to simultaneously advance the pair of endless bands.

27. The fastener delivery tool of claim 24, wherein the features comprise one of hooks and clips defining recesses configured to releasably receive the tines therein.

28. The fastener delivery tool of claim 24, wherein the features comprise nonmetallic material.

29. The fastener delivery tool of claim 24, further comprising a removable cover on the elongate shaft overlying the belt assembly.

30. The fastener delivery tool of claim 29, wherein the belt assembly is removably secured within the elongate shaft.

* * * * *